(12) United States Patent
Hammerlund

(10) Patent No.: US 11,911,787 B1
(45) Date of Patent: Feb. 27, 2024

(54) SPLIT MANIFOLD AND METHOD FOR MULTIPLE PART FLUID APPLICATIONS

(71) Applicant: Gary Hammerlund, Grand Rapids, MI (US)

(72) Inventor: Gary Hammerlund, Grand Rapids, MI (US)

( * ) Notice: Subject to any disclaimer, the term of this patent is extended or adjusted under 35 U.S.C. 154(b) by 576 days.

(21) Appl. No.: 16/995,442

(22) Filed: Aug. 17, 2020

Related U.S. Application Data

(60) Provisional application No. 62/888,008, filed on Aug. 16, 2019.

(51) Int. Cl.
*B05B 7/04* (2006.01)
*B05B 7/00* (2006.01)
(Continued)

(52) U.S. Cl.
CPC .......... *B05B 7/0408* (2013.01); *B05B 7/0018* (2013.01); *B29B 7/7447* (2013.01); *B29B 7/801* (2013.01); *F16K 15/145* (2013.01); *F16K 15/147* (2013.01); *F16K 15/1471* (2021.08); *F16K 15/1472* (2021.08); *F16L 37/56* (2013.01); *F16L 39/02* (2013.01); *F16L 41/023* (2013.01); *A61B 2017/00495* (2013.01); *Y10T 137/0402* (2015.04); *Y10T 137/87153* (2015.04)

(58) Field of Classification Search
CPC ..... B05B 7/0408; B29B 7/7447; B29B 7/801; F16K 15/147; F16K 15/145; F16K 15/1471; F16K 15/1472; A61B 2017/00495; F16L 37/56; F16L 39/02; F16L 41/023
See application file for complete search history.

(56) References Cited

U.S. PATENT DOCUMENTS 3,233,831 A    2/1966  Fraser
3,417,923 A    12/1968 Carlson
(Continued)

OTHER PUBLICATIONS

SynUthane International Inc. "Polyurethane Processing Equipment and Processing Overview." Understanding Polyurethanes (2002): F-1-67.
(Continued)

*Primary Examiner* — Atif H Chaudry
(74) *Attorney, Agent, or Firm* — Gardner, Linn, Burkhart & Ondersma LLP

(57) ABSTRACT

A fluid directing flow manifold for directing reactive fluids, independent of one another, from a dispensing manifold to a dispensing tip of a fluid dispensing apparatus provides a disposable and low cost fluid passageway between the dispensing manifold and dispensing tip while reducing or eliminating the possibility that reactive fluids will react and clog or block the dispensing manifold. The flow manifold provides independent fluid passageways between valves of a dispensing manifold and a mixing chamber of a dispensing tip of the dispensing apparatus. The flow manifold may be adapted for use with various types of fluid dispensing systems. The flow manifold may include multiple fluid guide bodies that may each be removed from the flow manifold to be cleaned or disposed of, and then replaced. Quick release mechanical fasteners are included for quick attachment of the manifold to a dispensing manifold valve and to the dispensing tip.

14 Claims, 13 Drawing Sheets

(51) Int. Cl.
*F16K 15/14* (2006.01)
*B29B 7/80* (2006.01)
*B29B 7/74* (2006.01)
*F16L 41/02* (2006.01)
*F16L 39/02* (2006.01)
*F16L 37/56* (2006.01)
*A61B 17/00* (2006.01)

(56) References Cited

U.S. PATENT DOCUMENTS

| | | | |
|---|---|---|---|
| 3,485,453 A | 12/1969 | Peeps | |
| 3,488,004 A | 1/1970 | Peeps | |
| 3,633,795 A | 1/1972 | Brooks | |
| 3,708,123 A | 1/1973 | Krueger | |
| 4,074,363 A | 2/1978 | Croft | |
| 4,245,784 A | 1/1981 | Garcin | |
| 4,516,725 A | 5/1985 | Cavanaugh et al. | |
| 4,549,676 A | 10/1985 | Gerich | |
| 4,643,336 A | 2/1987 | Mandeville et al. | |
| 4,666,086 A | 5/1987 | Cunningham | |
| 4,713,257 A | 12/1987 | Luttermöller | |
| 4,936,335 A | 6/1990 | Macon | |
| 5,033,655 A | 7/1991 | Brown | |
| 5,208,064 A | 5/1993 | Becker et al. | |
| 5,265,801 A | 11/1993 | Larson | |
| 5,312,042 A | 5/1994 | Larson | |
| 5,417,372 A | 5/1995 | Portugal | |
| 5,443,183 A * | 8/1995 | Jacobsen | B05C 17/00513 222/137 |
| 5,462,204 A | 10/1995 | Finn | |
| 5,529,245 A | 6/1996 | Brown | |
| 5,639,027 A | 6/1997 | Fritz | |
| 5,740,965 A | 4/1998 | Miyagi et al. | |
| 5,799,876 A | 9/1998 | Isler | |
| 5,810,885 A | 9/1998 | Zinger | |
| 5,893,486 A | 4/1999 | Wasmire | |
| 6,021,961 A | 2/2000 | Brown | |
| 6,165,201 A | 12/2000 | Sawhney et al. | |
| 6,234,666 B1 | 5/2001 | Kolb | |
| 6,283,221 B2 | 9/2001 | Hurray et al. | |
| 6,345,776 B1 | 2/2002 | Hurray et al. | |
| 6,375,096 B1 | 4/2002 | Rashidi | |
| 6,461,325 B1 | 10/2002 | Delmotte et al. | |
| 6,527,203 B2 | 3/2003 | Hurray et al. | |
| 6,601,782 B1 | 8/2003 | Sandholm et al. | |
| 6,835,186 B1 | 12/2004 | Pennington et al. | |
| 6,840,462 B2 | 1/2005 | Hurray et al. | |
| 6,884,232 B1 | 4/2005 | Hagmann et al. | |
| 7,140,558 B2 | 11/2006 | McCracken et al. | |
| 7,559,440 B2 | 7/2009 | Rueschhoff et al. | |
| 7,717,357 B2 * | 5/2010 | Gantenbein | E04F 21/12 239/432 |
| 7,918,369 B2 | 4/2011 | Kosmyna et al. | |
| 9,085,002 B2 | 7/2015 | Zimmerman et al. | |
| 9,089,869 B2 | 7/2015 | Galvin et al. | |
| 9,174,234 B2 | 11/2015 | Snowwhite et al. | |
| 9,242,846 B2 | 1/2016 | Burns | |
| 9,314,749 B2 | 4/2016 | Yagi et al. | |
| 9,566,594 B2 | 2/2017 | Galvin et al. | |
| 9,573,150 B2 | 2/2017 | Snowwhite et al. | |
| 9,610,604 B2 | 4/2017 | Galvin et al. | |
| 10,639,656 B1 | 5/2020 | Hammerlund | |
| 2002/0165483 A1 | 11/2002 | Miller et al. | |
| 2003/0209612 A1 | 11/2003 | Hahnen | |
| 2004/0240311 A1 | 12/2004 | Hashiba | |
| 2005/0087623 A1 | 4/2005 | Finn | |
| 2006/0208000 A1 * | 9/2006 | Murray | B29B 7/7404 222/145.5 |
| 2008/0031081 A1 | 2/2008 | Rigolio | |
| 2008/0144426 A1 | 6/2008 | Janssen et al. | |
| 2010/0065130 A1 | 3/2010 | Swab et al. | |
| 2010/0065660 A1 | 3/2010 | Hull et al. | |
| 2010/0065768 A1 | 3/2010 | Swab et al. | |
| 2010/0096481 A1 | 4/2010 | Hull et al. | |
| 2011/0209780 A1 | 9/2011 | Gantenbein et al. | |
| 2011/0319930 A1 | 12/2011 | Roush et al. | |
| 2012/0158048 A1 | 6/2012 | Roush et al. | |
| 2013/0028841 A1 | 1/2013 | Yagi et al. | |
| 2013/0221135 A1 | 8/2013 | Myers | |
| 2013/0269806 A1 | 10/2013 | Burns | |
| 2014/0107620 A1 | 4/2014 | Fech et al. | |
| 2014/0117116 A1 | 5/2014 | Masson et al. | |
| 2014/0263749 A1 | 9/2014 | Davis et al. | |
| 2015/0085601 A1 | 3/2015 | Hammerlund | |
| 2015/0124554 A1 | 5/2015 | Haden et al. | |
| 2016/0184847 A1 | 6/2016 | Hammerlund | |
| 2017/0095823 A1 | 4/2017 | Goisot et al. | |

OTHER PUBLICATIONS

Plas-Pak Industries, Inc. "Ratio-Pak® High Flow Threaded Static Mixers." Copyright 2009. Web. Oct. 9, 2016. http://plaspakinc.com/ratiopak-staticmixers.php.

OMG Roofing Products. "OMG Pace Cart 2 for Olybond500 Owner's Manual." Patented portable delivery system for OlyBond 500 Insulation Adhesive featuring patented bag-in-box technology. pp. 1-6. Copyright 2014.

Nordson EFD. "400 Autovalve Pneumatic Instructions/Parts List." Copyright 2015. Nordson Corporation. pp. 1-24.

Adco Roofing Products. "Millennium Cyclone 1 Low Pressure Pump Cartby Garlock." Product Information, believed to have been published prior to Oct. 16, 2015.

Cartridge Dispensing and Static Mixing List of Do's and Don'ts. Guidelines for Determining Appropriate Cartridges and Static Mixers for Dispensing Applications, believed to have been published prior to Oct. 16, 2015.

\* cited by examiner

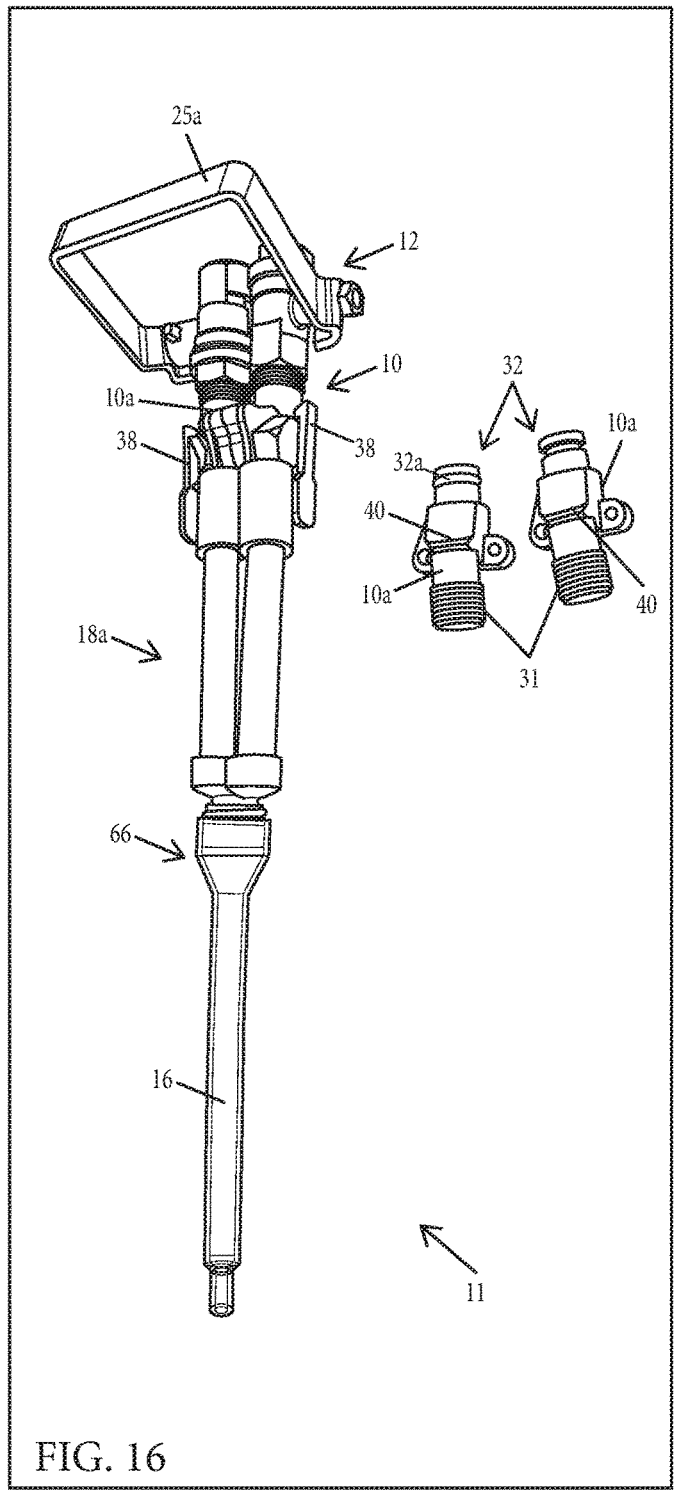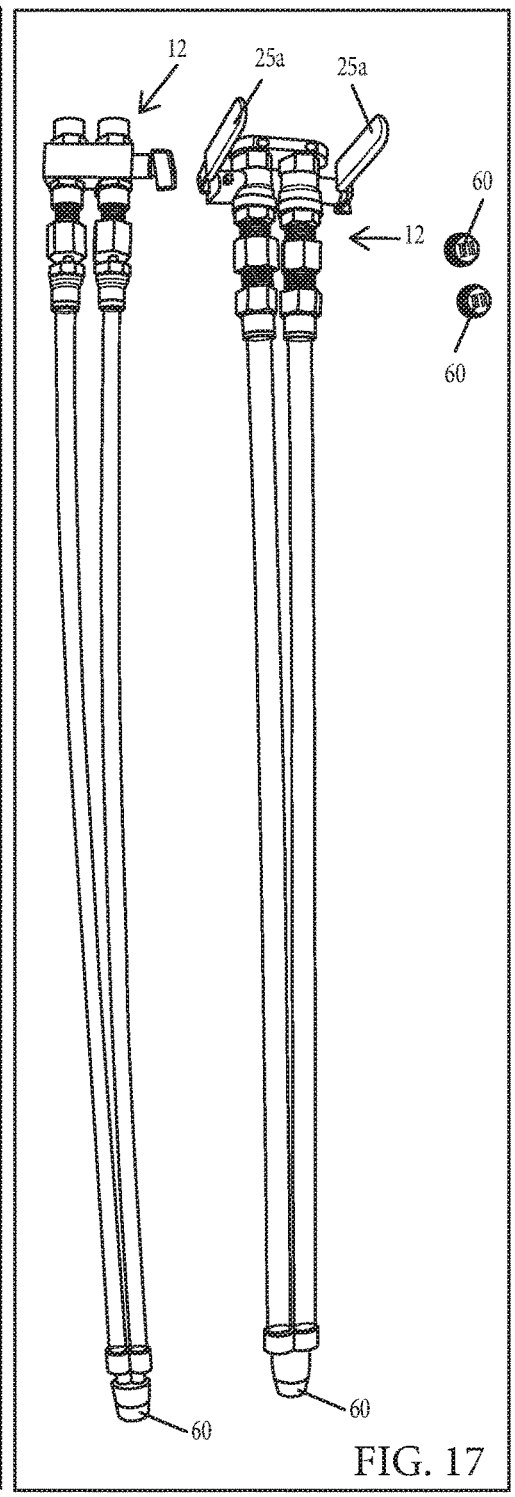
FIG. 16
FIG. 17

SPLIT MANIFOLD AND METHOD FOR MULTIPLE PART FLUID APPLICATIONS

CROSS REFERENCE TO RELATED APPLICATION

The present application claims the benefit of U.S. provisional application Ser. No. 62/888,008, filed Aug. 16, 2019, which is hereby incorporated herein by reference in its entirety.

FIELD OF THE INVENTION

The present invention is directed to fluid dispensing apparatuses for multi-part fluid application, and more particularly, to components for attachment to spray guns or dispensers that are used for simultaneously mixing and discharging two or more fluid substances, such as for dispensing adhesives, two-part polyurethane foam insulation, and the like.

BACKGROUND OF THE INVENTION

Multi-component mixing and dispensing systems are commonly used to spray or otherwise dispense highly reactive fluids that are stored in separate containers and that flow under low or high pressure through separate fluid lines to a dispensing manifold having an on/off valve, and having a mixing nozzle (often a disposable piece) located downstream of the on/off valve. Because a chemical reaction is initiated as soon as the reactive fluids come into contact with one another, the on/off valve must generally be turned on with sufficient frequency so that the mixed fluids do not have sufficient time to harden to a point where they would block flow through the nozzle. This condition can occur quickly and may result in significant down-time for the dispensing gun to be at least partially disassembled and manually cleaned out with tools and solvents, before re-assembly and re-use.

Spray guns or dispensing manifolds are typically used for simultaneously mixing and discharging two or more fluid components, and include nozzles or tips through which the fluid components are discharged. For example, thermal insulation and adhesives used in building construction may be sprayed through a manifold that receives two different liquid components which, when mixed together, react and begin to cure as a rigid or semi-rigid foam material after the reaction is complete. The fluids are discharged through a nozzle in a partially-reacted state, and are discharged against a surface (such as a wall surface, roof, packaging, or the like), where the components stick and remain substantially in place while the reaction completes to form the cured substance along the desired surfaces.

Because the reacting fluids are at least partially mixed together inside a dispensing nozzle of the dispensing manifold, cured or curing foam product will typically build up inside the nozzle, particularly when the flow of fluids is stopped during temporary periods of non-use. This can lead to rapid clogging of the tip, which typically necessitates a cleaning step (e.g., discharging acetone or other chemical solvent through the tip, drilling out the cured substance, etc.). Although cleaning procedures may be used to clear clogged tips, they also require extra time and may present health and/or environmental hazards around the operator applying the fluids. An example of a dispensing manifold of the type described above includes U.S. Pat. No. 9,242,846, issued Jan. 26, 2016. Such system configurations and associated dimensions and geometries often create restrictions on a fluid flow that can decrease the flow rate of fluid dispensed from the dispensing manifold.

Some high pressure spray systems (e.g., those operating at 250 psi or greater) have been developed that at least partially address the problem of cured materials clogging the spray nozzles or tips; however, such high pressure systems are typically far more expensive than comparatively lower pressure systems (e.g., those operation at less than 250 psi), can be substantially more complex and expensive to purchase and operate, and can require substantially more training for operators and more costly personal protective equipment ("PPE"). Even with typical low pressure systems, the time required to change or clean clogged tips increases the overall cost of operating the equipment, particularly since clogs may develop in as little as a few seconds of non-use.

SUMMARY OF THE INVENTION

The present invention provides a removable and disposable flow manifold to independently direct flows from at least two sources of fluid from a valve body, dispensing manifold or spray gun toward a mixing and dispensing tip, such that the fluids do not interact with each other until they have entered the mixing and dispensing tip. The flow manifold is resistant to reactive fluids used in spray adhesives and foams as well as cost-effective and optionally disposable to allow for removing the flow manifold and replacing it to reduce cleaning and maintenance time required in the event that reactive fluids react and clog inside of a valve of the dispensing manifold. The flow manifold is configurable to couple to various types of dispensing manifolds, spray guns, and valve bodies. The flow manifold may include multiple fluid guide bodies that may each be removed from the flow manifold to be cleaned or disposed of, and then replaced, as required.

In one form of the present invention, a split manifold system is provided for independently directing reactive fluids from a spray gun, dispensing manifold, or valve body toward a dispensing tip. The split manifold includes a manifold body that includes at least two independent fluid passageways to each direct or guide a reactive fluid from a valve toward the dispensing tip. The fluid passageways include a fluid inlet to receive a fluid from a corresponding valve in the valve body and a fluid outlet to discharge that fluid to the dispensing tip. The split manifold ensures that each reactive fluid remains independent of other reactive fluids before reaching a downstream mixing zone, to reduce or eliminate the possibility of the fluids reacting at the dispensing manifold and clogging or blocking fluid passageways of the dispensing manifold. The split manifold can be removed from the valve body, disposed of, and replaced with a clean split manifold, while the reactive fluids remain separated from each other in proximity to the valve body. The split manifold body includes a mechanical coupling element to secure the flow manifold to the valve body, as well as a mechanical coupling element to secure the flow manifold to the dispensing tip.

In one aspect, a fluid guide body is disposed between each valve of the valve body and the dispensing tip. The fluid guide bodies may be configured to couple to a variety of different spray guns, dispensing manifolds, and valve bodies. The fluid guides may include various mechanical fastener types to accommodate the various types of manifolds, valves, or guns, including threaded fasteners, slip-plug fasteners, or the like.

In another aspect, the flow manifold includes a manifold extension to extend the reach of the dispensing manifold. The manifold extension may be coupled at an upstream end directly to a valve of the dispensing manifold and at the downstream end to the inlet of the flow manifold or at the upstream end to a discharge end of the flow manifold and coupled at a downstream end directly to the dispensing tip. The manifold extension may be provided in various lengths to accommodate various applications, such as applying paint, roofing adhesive, or the like, which require precise application of the mixed fluid. The manifold extension includes fluid passageways through elongated tubes, the inner diameters of the elongated tubes are selected such that the fluid flowing through the passageway is substantially unrestricted.

In yet another aspect, the flow manifold includes a crossover prevention valve disposed at a discharge end of the flow manifold to further prohibit or eliminate interaction between the reactive fluids at or near the dispensing manifold, spray gun, or valve. The crossover prevention valve includes one way valves that prohibit back flow of fluid through the valve.

In still another aspect, the fluid outlet ends of the flow manifold may have different diameters to accommodate various fluid consistencies or to control the volume and pressure of the discharge of the fluid. The diameter of each fluid outlet is determined based on a function of material characteristics of the composition of the fluid being directed through that fluid outlet.

In another form of the present invention, the flow manifold is assembled from two or more fluid guide bodies that are mechanically fastened together. Each fluid guide body includes an independent fluid passageway to guide a fluid from a corresponding valve in the valve body to the dispensing tip. The assembly of fluid guide bodies can be disassembled and each guide body can be disposed of and replaced, or one or more of the guide bodies can be reused while the other, or others, are replaced to accommodate a new fluid or to replace a clogged guide body.

Optionally, each fluid guide body includes at least a portion of a mechanical fastener that is configured to secure the flow manifold to the valve body or to the dispensing tip. For example, each fluid guide body may include a portion of threads at an outlet end of the assembled manifold, such that when the fluid bodies are assembled together to form the flow manifold, the respective portions of threads form a male threaded fastener end configured to threadedly engage female threads at the inlet end portion of the dispensing tip.

In one aspect, the fluid guide bodies are identical to one another, and are shaped and configured so that respective identical portions of two fluid guide bodies interlock with one another during assembly to form the assembled manifold.

In another aspect, an additional manifold body is provided between the flow manifold and the dispensing tip. The additional manifold may include a unitary body defining a plurality of fluid inlets and a plurality of fluid outlets. The additional manifold provides an interface between a plurality of fluid guide bodies and the dispensing tip such that the additional manifold can be quickly removed from either the flow manifold or the dispensing tip to be cleaned or replaced. The additional manifold may include a push-to-connect mechanical fastener system to releasably attach the additional manifold to the flow manifold or to the dispensing tip.

Therefore, the split manifold of the present invention provides a low-cost and disposable flow directing manifold to independently direct or guide reactive fluids from a respective dispensing manifold valve to a dispensing tip of a spray gun or dispensing manifold apparatus such that the reactive fluids do not react with one another proximate the dispensing manifold valve, which might clog or block the valve. The flow manifold reduces down time associated with cleaning clogs in the valves or dispensing manifold components due to the reactive fluids having reacted in or near the valves or components, which can occur in a just short period of time if the dispensing manifold is not operating. The flow manifold ensures that the reactive fluids do not interact with one another until they have reached a desired location, such as a mixing chamber in the mixing and dispersing tip of a dispensing manifold apparatus. The flow manifold may be configured such that portions or components of the flow manifold may be removed or replaced independent of the other components of the flow manifold, thereby reducing downtime for maintenance and reducing costs of materials associated with cleaning or reconfiguring the dispensing manifold.

These and other objects, advantages, purposes, and features of the present invention will become more apparent upon review of the following specification in conjunction with the drawings.

BRIEF DESCRIPTION OF THE DRAWINGS

FIG. 16 is a perspective view of a split manifold for a dispensing manifold in accordance with the present invention, including an additional pair of fluid guide bodies shown disassembled;

FIG. 17 is a perspective view of various embodiments and components of a split manifold for a dispensing manifold in accordance with the present invention:

DESCRIPTION OF THE PREFERRED EMBODIMENTS

Figure 1:
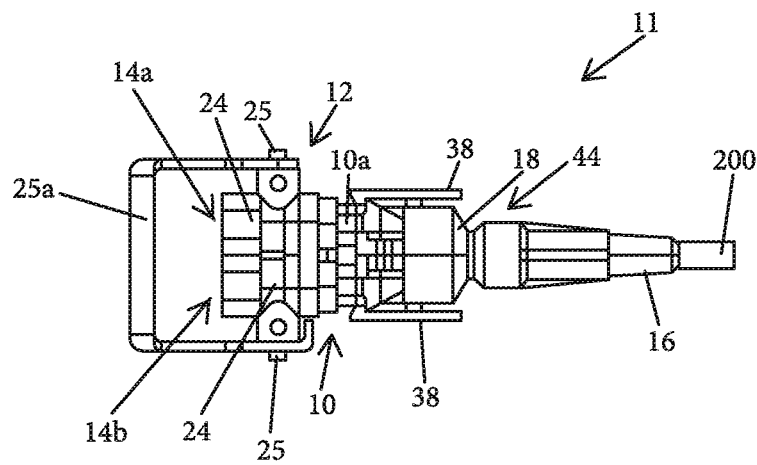
FIG. 1 is a top view of a split manifold assembly for a dispensing manifold in accordance with the present invention.
Figure 2:
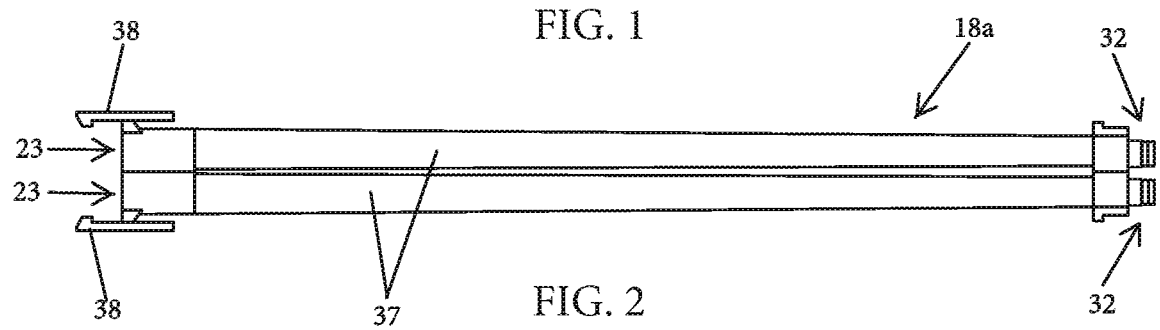
FIG. 2 is a top plan view an extension manifold compatible for use with the split manifold assembly of FIG. 1.
Figure 3:
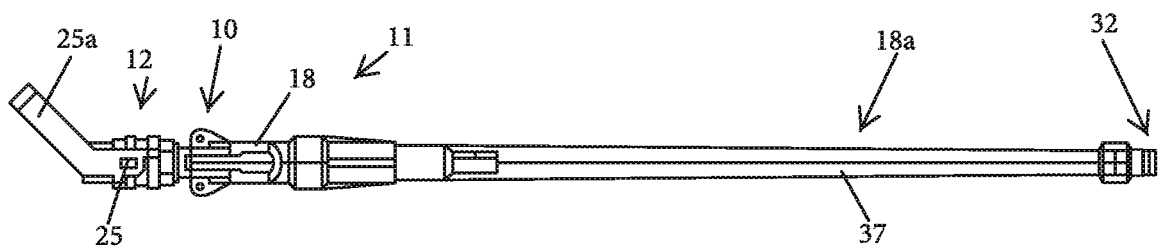
FIG. 3 is a side elevation of the split manifold assembly of FIG. 1, shown coupled to extension tubes of FIG. 2.
Figure 4:
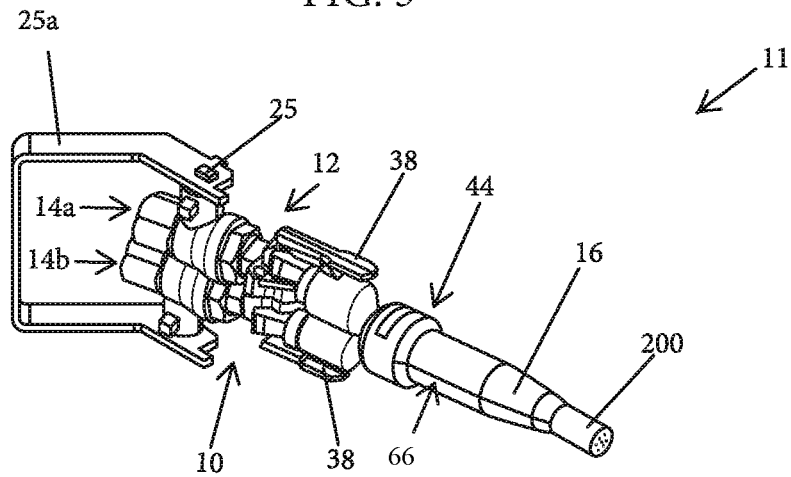
FIG. 4 is a perspective view of the split manifold assembly of FIG. 1.

Referring now to the drawings and the illustrative embodiments depicted therein, a disposable flow directing manifold or split manifold 10 is fitted to a valve portion 12 of a dispensing manifold 11 at a discharge end portion of the valve portion 12. (FIG. 1). In the illustrated embodiment, the split manifold 10 is designed for use with a dispensing manifold 11 for mixing and discharging two different reactive fluids (typically liquids) that combine and react to form a final product, such as roofing adhesive, insulating foam, packing foam, paint, or the like. However, it will be appreciated that other flow manifolds may be configured for use with three or more reactive fluids in accordance with other embodiments, without departing from the spirit and scope of the present invention. The split manifold 10 is compatible for use with a multi-component fluid mixing and dispensing manifold system 11 that includes a dispensing valve portion 12 configured to receive and convey two different fluid reactants from respective fluid sources along a pair of independent conduits or passageways 14 to an end fitting, such as a dispensing nozzle or dispensing tip 16. The split manifold 10 may be coupled with an additional manifold or coupling element, such as a push-to-connect manifold 18, configured to provide a quick-disconnect coupler between the split manifold 10 and the dispensing nozzle 16. It will be appreciated that dispensing manifold 11 is representative of substantially any common or known dispensing manifold, gun, valve, or apparatus capable of conveying two or more fluids along separate and isolated flow paths until a point or region at which they are to be mixed and/or discharged, and that the principles of the present invention may be adapted for use with substantially any desired dispensing system for two or more separate fluid streams.

The split manifold 10 of the illustrated embodiments provides a disposable fluid directing manifold including independent flow passages 14 for directing two reactive fluids from a valve portion 12 of a dispensing manifold 11 to a push-to-connect manifold 18, and to a dispensing tip 16 (FIGS. 1, 3-6). The split manifold 10 and push-to-connect manifold 18 provide a replaceable buffer or distance between the valve portion 12 and a location where two reactant fluids are to be mixed and begin reacting. The split manifold 10 allows a user to remove, dispose of, and replace the components of the dispensing manifold 11 (i.e. split manifold 10, valve 12, push-to-connect manifold 18) to reduce or eliminate down time and cleaning of the components of the dispensing manifold 11 due to curing of the reacted fluids inside of or on surfaces of the components.

Figure 12A:
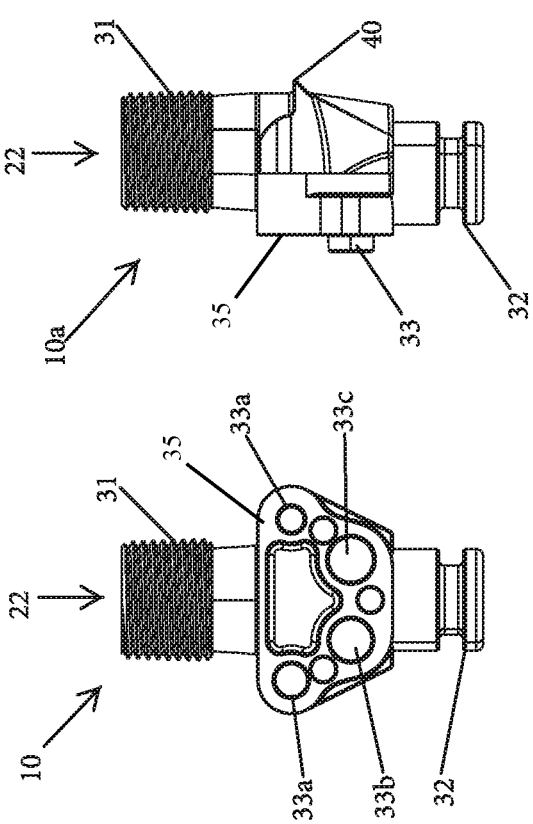
FIGS. 12A-12C are side elevation views of a fluid guide body configured to form one half of a split manifold in accordance with the present invention.
Figure 12B:
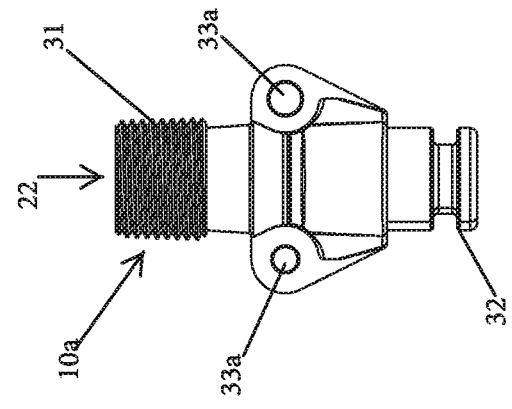
Figure 12C:
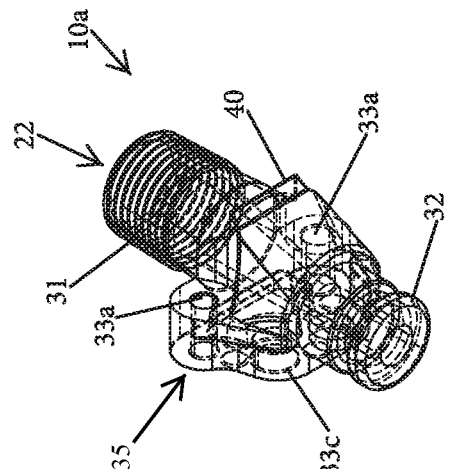
Figure 12D:
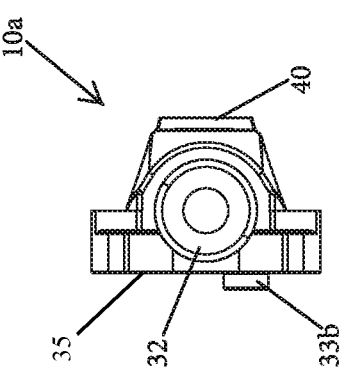
FIG. 12D is an end elevation of a discharge end of the fluid guide body of FIGS. 12A-12C.
Figure 12E:
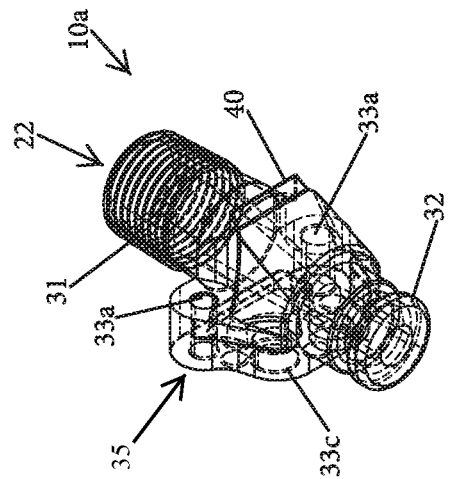
FIG. 12E is a perspective view of the fluid guide body of FIGS. 12A-12D, shown in transparency.
Figure 13A:
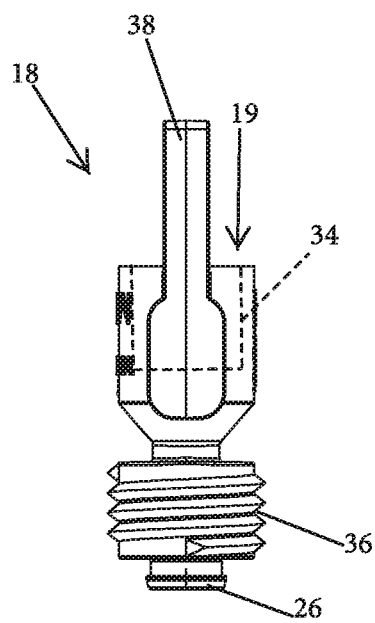
FIG. 13A is a side elevation of a push-to-connect manifold in accordance with the present invention.
Figure 13B:
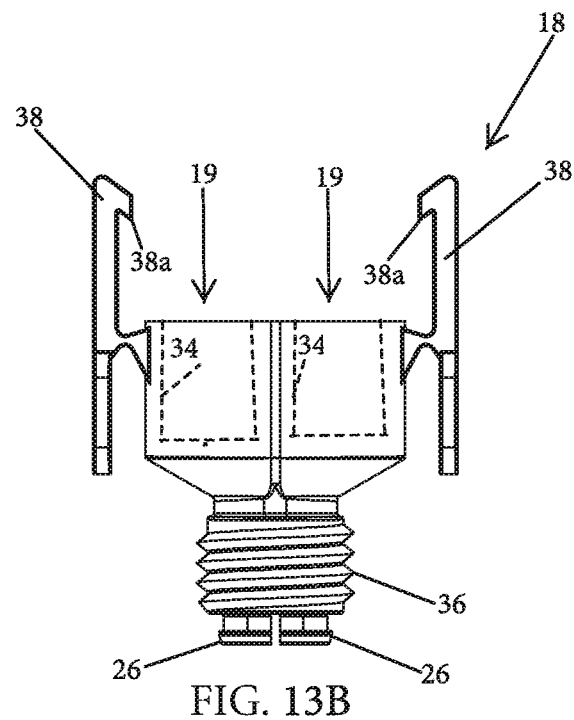
FIG. 13B is a top elevation of the push-to-connect manifold of FIG. 13A.
Figure 13C:
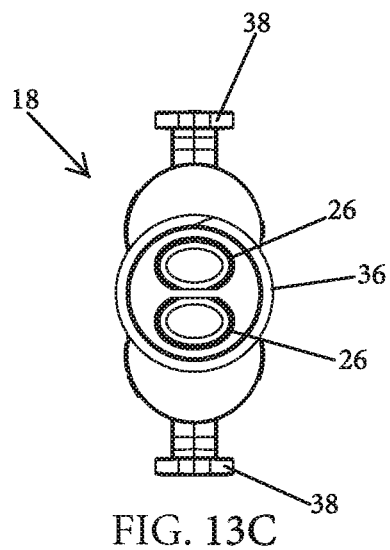
FIG. 13C is an end elevation of a discharge end of the push-to-connect manifold of FIG. 13A.
Figure 13D:
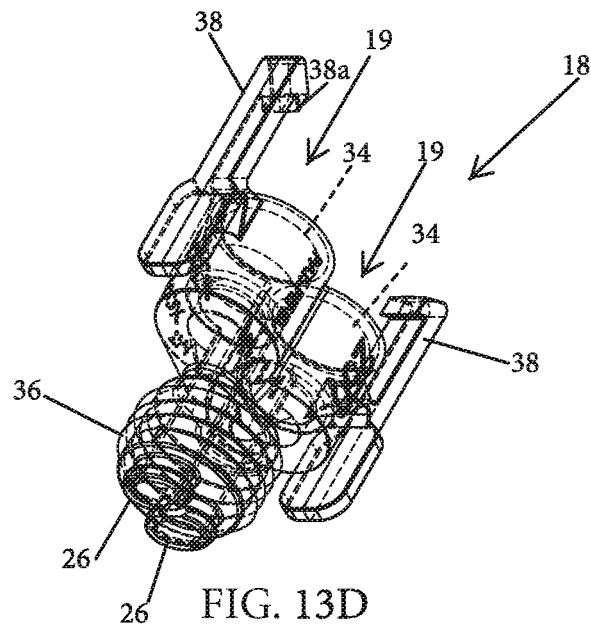
FIG. 13D is a perspective view of the push-to-connect manifold of FIG. 13A, shown in transparency.
Figure 14A:
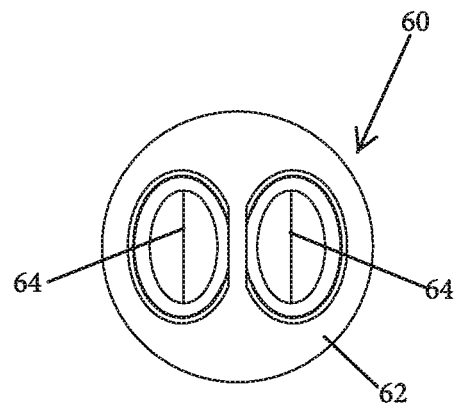
FIG. 14A is an end elevation of an inlet end of a crossover prevention valve compatible for use with the push-to-connect manifold of FIGS. 13A-13D.
Figure 14B:
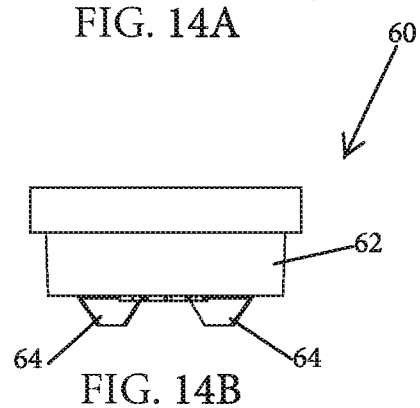
FIGS. 14B and 14C are side elevations of the crossover prevention valve of FIG. 14A.
Figure 14C:
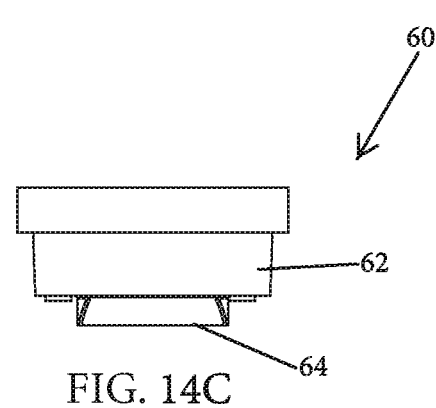
Figure 14D:
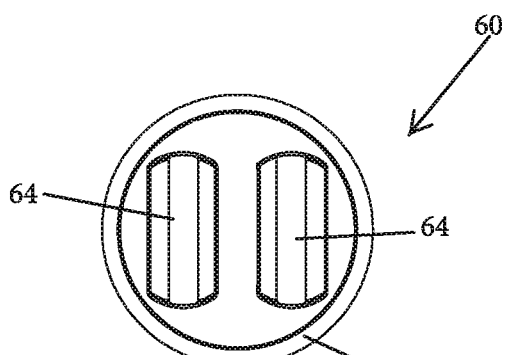
FIG. 14D is an end elevation of a discharge end of the crossover prevention valve of FIG. 14A.
Figure 14E:
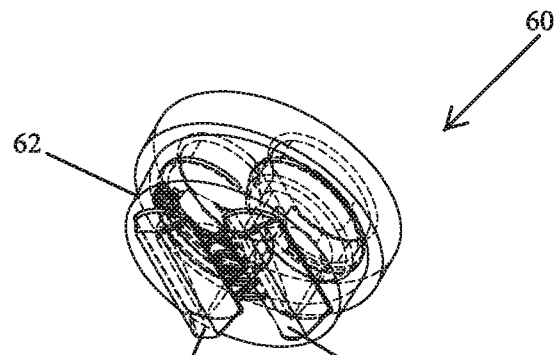
FIG. 14E is a perspective view of the crossover prevention valve of FIGS. 14A-14D, shown in transparency.
Figure 15A:
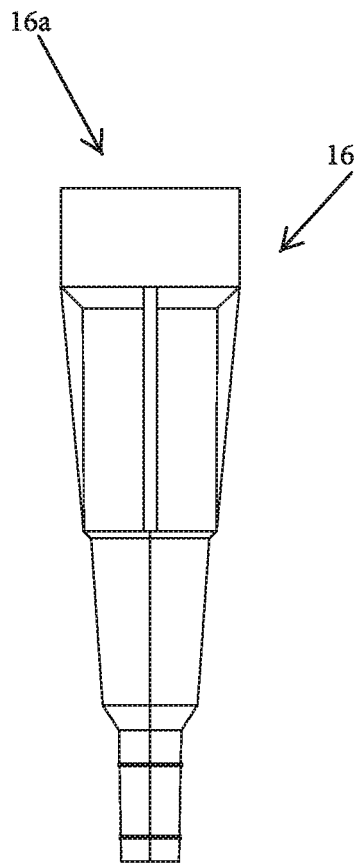
FIGS. 15A and 15B are side elevations of a mixing tip compatible for use with the split manifold.
Figure 15B:
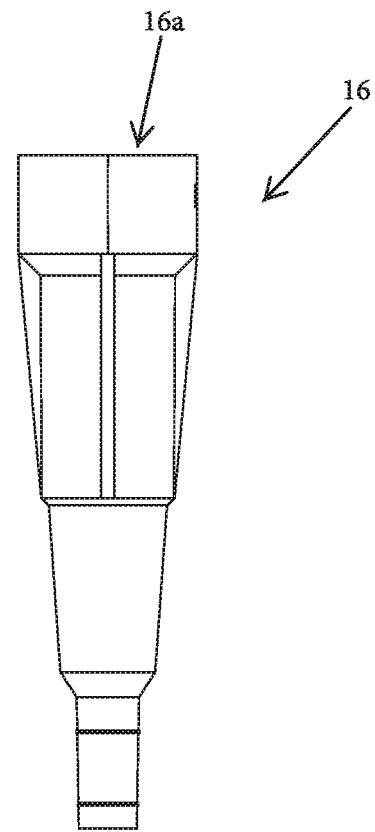
Figure 15C:
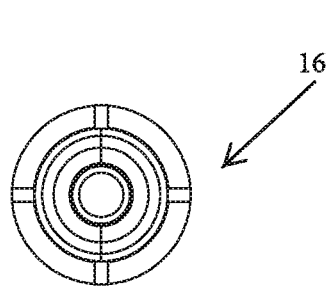
FIG. 15C is an end elevation of a discharge end of the mixing tip of FIGS. 15A and 15B.
Figure 15D:
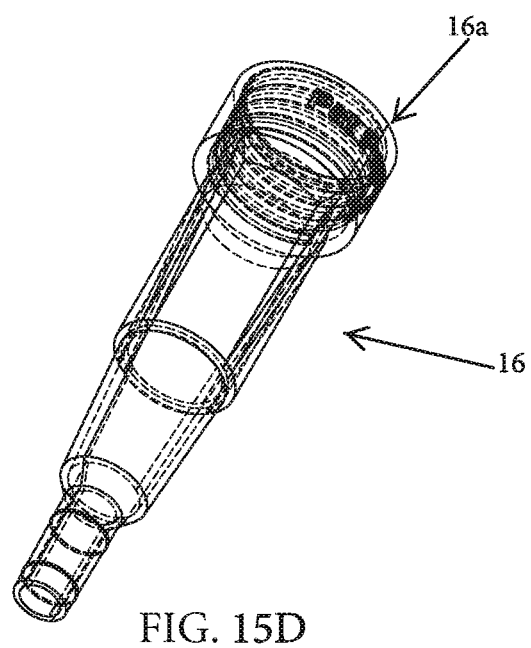
FIG. 15D is a perspective view of the mixing tip of FIGS. 15A-15C, shown in transparency.
Figure 18:
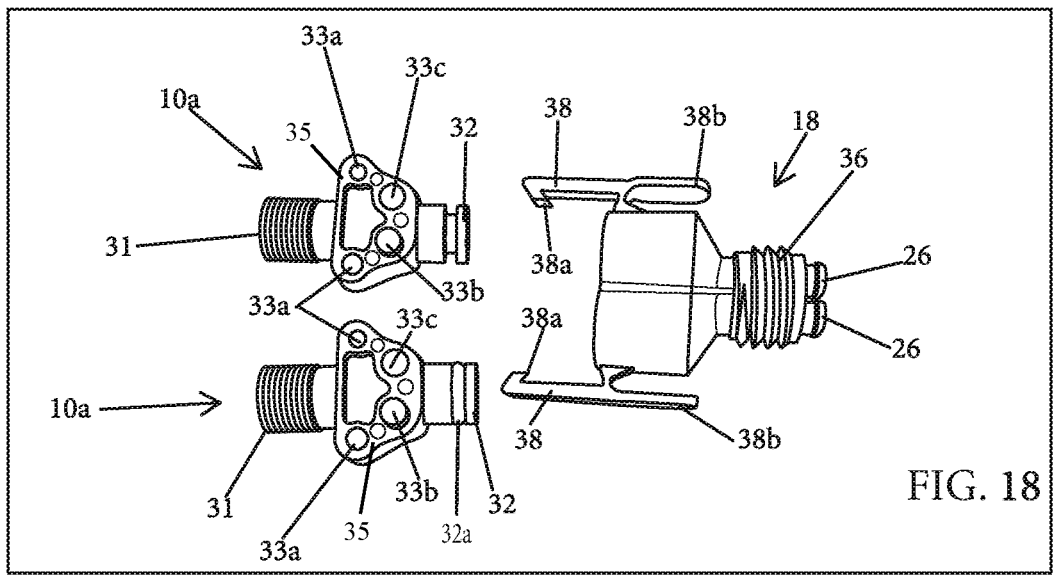
FIG. 18 is an exploded perspective view of a pair of separated fluid guide bodies of FIGS. 12A-12E and push-to-connect manifold of FIGS. 13A-13D.

The valve portion 12 includes a first fluid inlet 14a for receiving a first fluid from a first fluid source (not shown), and similarly includes a second fluid inlet 14b for receiving a second fluid from a second fluid source (not shown). First and second fluid inlets 14a, 14b lead to respective first and second fluid passageways 20a, 20b through the valve 12 body, which direct respective fluids toward fluid passageways 22 in the split manifold 10 when a valve rod 25 of a fluid valve 24 is moved to a flow position (FIGS. 12A-12C). For example, valve rod 25 may typically be rotated by a handle or lever 25a or the like located on the valve portion 12, with the valve rod 25 itself permitting fluid flow through passageways in the rod, or actuating retractable valve rods. The first and second fluids pass through their respective fluid passageways 22 in the split manifold 10. The fluids proceed through respective fluid passageways 19 (FIGS. 13A-13B) of the push-to-connect manifold 18 and out of orifices 26a, 26b and into a dispensing nozzle 16, substantially without the fluids interacting inside the split manifold 10 or push-to-connect manifold 18.

Figure 5:
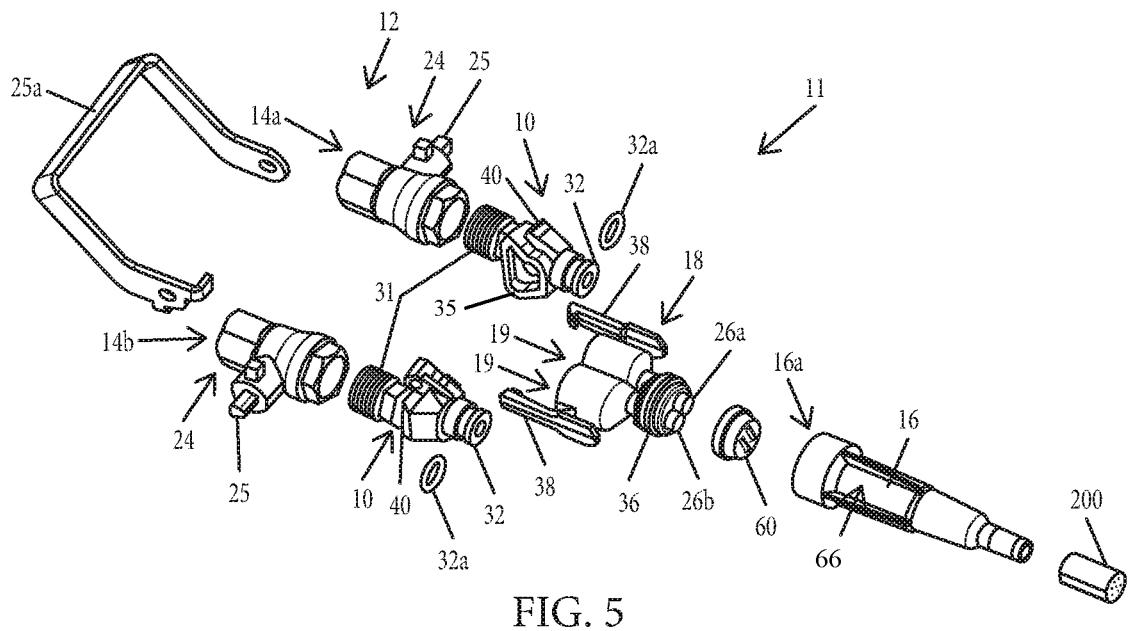
FIG. 5 is an exploded perspective view of the split manifold assembly of FIG. 1.
Figure 6:
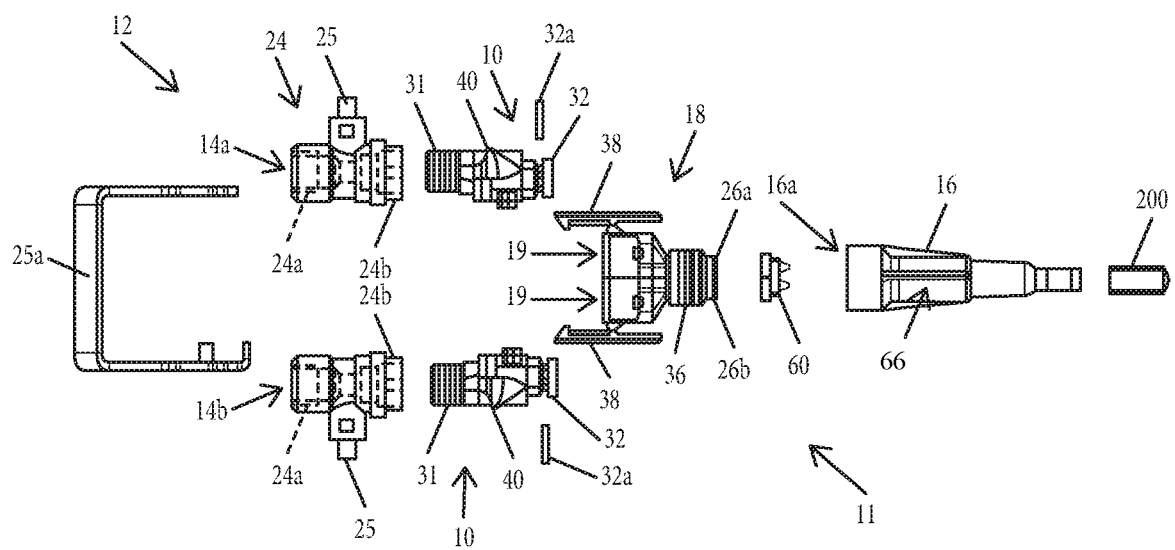
FIG. 6 is an exploded top plan view of the split manifold assembly of FIG. 1.
Figure 7:
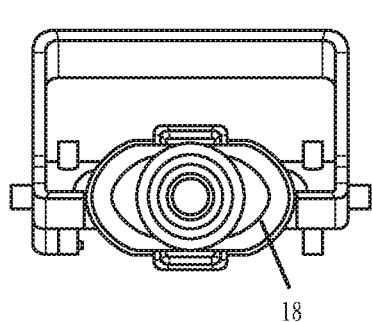
FIG. 7 is a front elevation of the split manifold assembly of FIG. 1.
Figure 8:
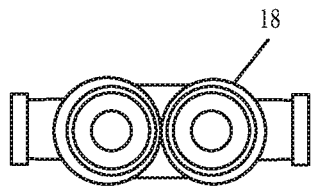
FIG. 8 is a rear elevation of the split manifold of FIG. 1.
Figure 9:
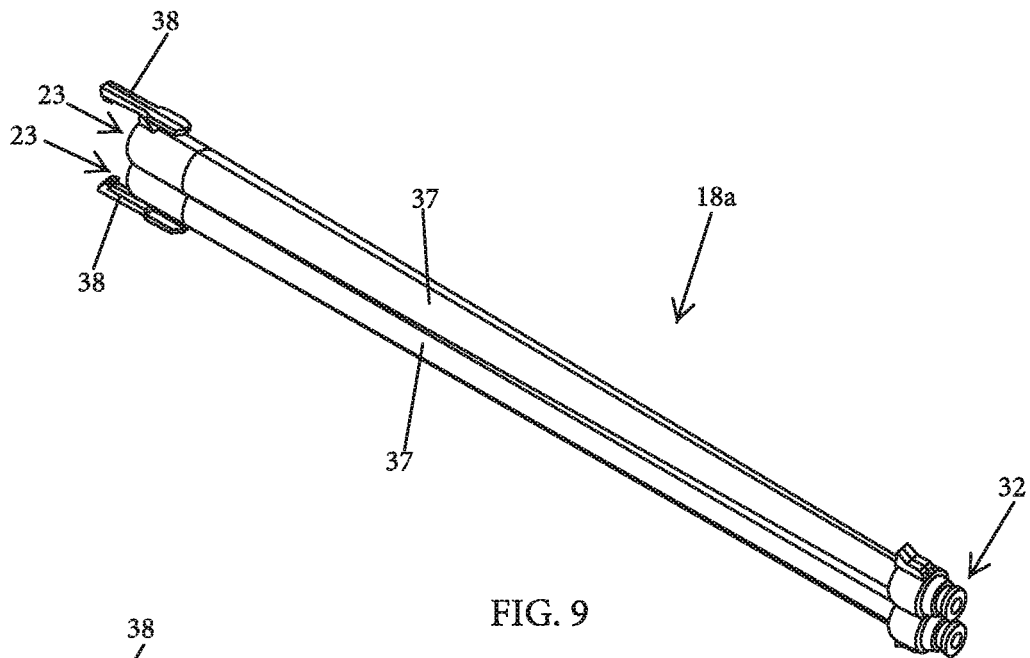
FIG. 9 is a perspective view of the extension manifold of FIG. 2.
Figure 10:
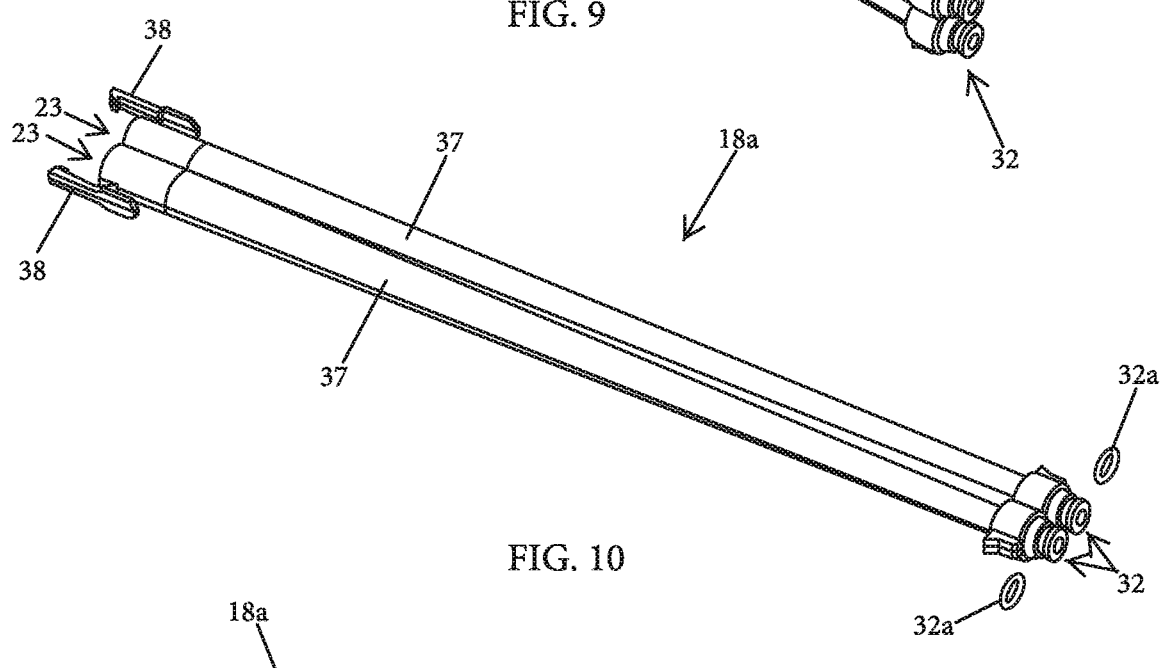
FIG. 10 is another perspective view of the extension manifold of FIG. 2, depicting O-ring seals separated from a slip-plug.
Figure 11:
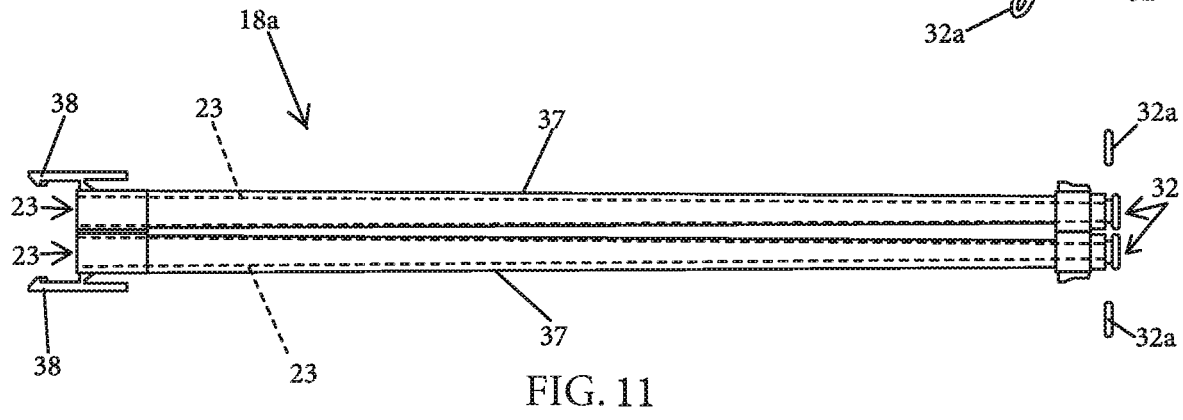
FIG. 11 is a top plan view of the extension manifold of FIG. 10, with inner fluid passageways shown in phantom.

In the illustrated embodiments of FIGS. 1, 3-6, 16, 18-20, and 29-31, split manifold 10 includes an assembly of split fluid guide bodies 10a to connect each fluid valve 24 of the valve portion 12 to a corresponding fluid passageway 19 of the push-to-connect manifold 18. Each fluid guide 10a includes a male threaded inlet 31 at the proximal end portion and a male slip-plug 32 at the discharge end portion of the fluid guide 10a. The male threaded inlet end portion 31 is configured to threadedly engage female threads at an outlet end portion 24b of each valve 24. The male slip-plug 32 (best shown in FIGS. 12A-12E) is configured to slidingly engage a female slip socket or tube receptacle 34 (best shown in FIGS. 13A-13D) at a proximal end portion of the push-to-connect manifold 18. An O-ring 32a is included with each slip-plug 32 to fluidly seal between slip-plug 32 and tube receptacle 34 (FIGS. 5-6). The split manifold 10 includes a dispensing coupling element, such as slip plugs and push-to-connect fittings as shown in FIGS. 1, 3-6, 16, 18-20, and 29-31 or such as a male threaded distal end portion 136 as shown in FIGS. 21-24 which are configured to threadedly engage female threads at the inlet end portion 16a of the dispensing nozzle 16 to couple the split manifold 10 to the dispensing nozzle 16. The threaded distal end portion 136 of FIGS. 21-24 are discussed in further detail below. The optional push-to-connect manifold 18 of the illustrated embodiments includes a male threaded distal end portion 36 configured to threadedly engage female threads at the inlet end portion 16a of the dispensing nozzle 16 to couple the push-to-connect manifold 18 to the dispensing nozzle 16 (FIGS. 1, 3-6, 13A-13D, 18-20, 25, 27-31). Although threaded and/or slip connections are discussed herein, it will be appreciated that other types of mechanical connections may be utilized for attachment between the valve portion 12, dispensing nozzle 16, fluid guides 10a, and push-to-connect manifold 18.

In the illustrated embodiment of FIGS. 2-3 and 9-11, an elongated manifold extension 18a is provided and includes elongated tubes 37 having female tube receptacles 34 at a proximal end and male slip-plugs 32 at a distal end. The elongated tubes 37 include inner fluid passageways 23 for directing fluids through the manifold extension 18a (FIGS. 2, and 9-11). The extension 18a provides for increased reach or range between the valve portion 12 and the surface or area to be sprayed. The manifold extension 18a may be coupled at a proximal end directly to the valve portion 12 and at a distal end to the inlet of the split manifold 10 or preferably at the proximal end to a discharge end of the split manifold 10 and coupled at the distal end directly to the dispensing tip 16. The manifold extension 18a may be provided in various lengths to accommodate various applications, such as applying paint, roofing adhesive, or the like, which require precise application of the mixed fluid. The geometry and diameters of the elongated tubes 37 are selected to substantially reduce restriction of fluid flow through the tubes 37 such that the volume of dispensed fluid from the dispensing manifold 11 is substantially not reduced by the use of the manifold extension 18a.

Figure 19:
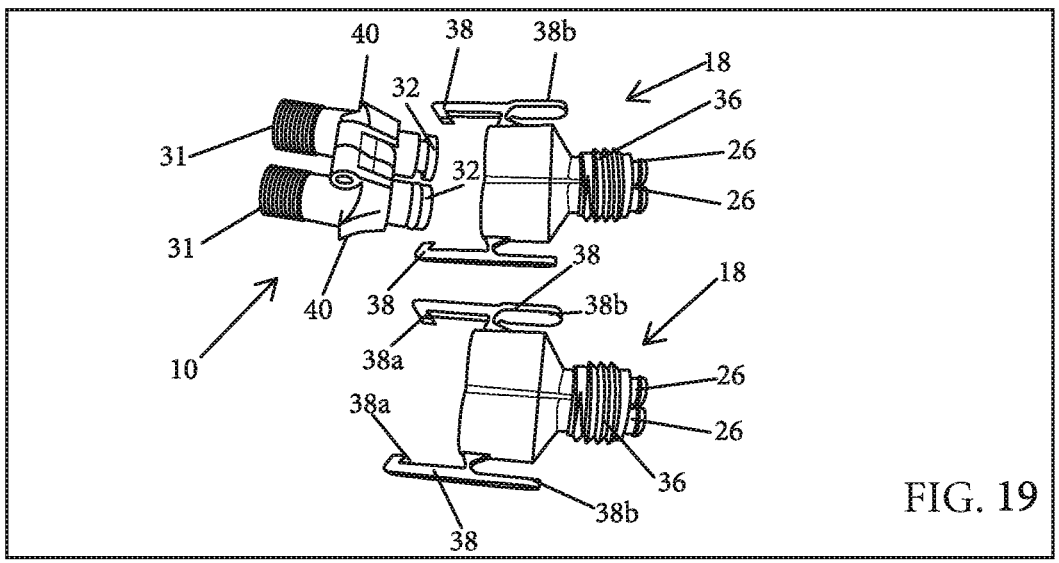
FIG. 19 is a partially exploded perspective view of the fluid guide bodies assembled together and a pair of push-to-connect manifolds of FIG. 18.
Figure 20:
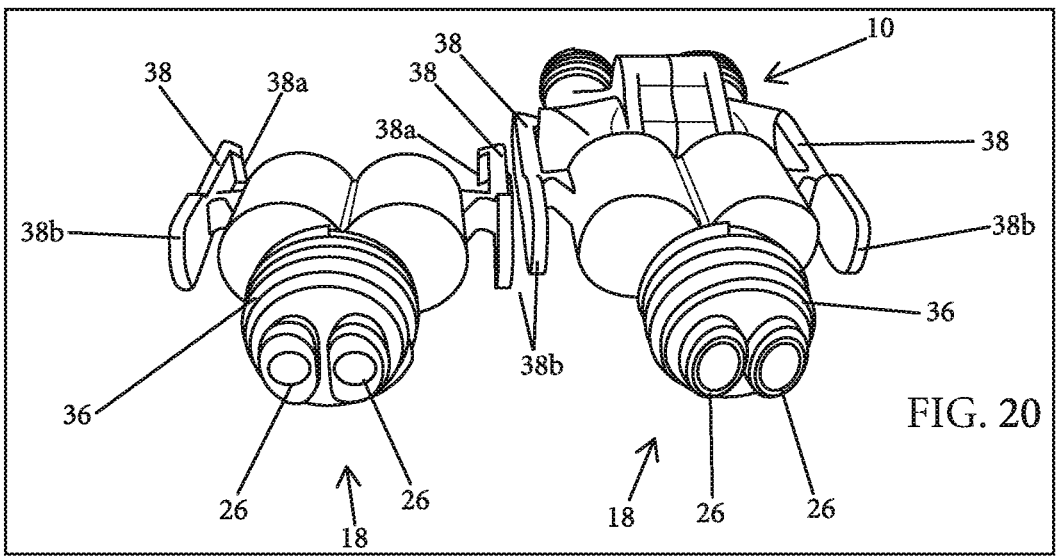
FIG. 20 is another a perspective view of the discharge ends of a pair of push-to-connect manifolds of FIGS. 13A-13D, one of which is fitted with assembled fluid guide bodies of the split manifold.
Figure 23:
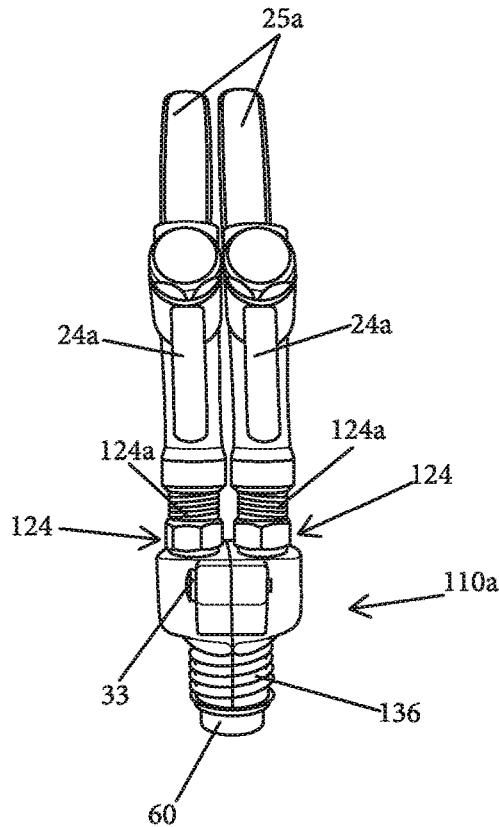
FIG. 23 is a perspective view of the split manifold of FIG. 21 shown coupled to a trigger valve apparatus.
Figure 24:
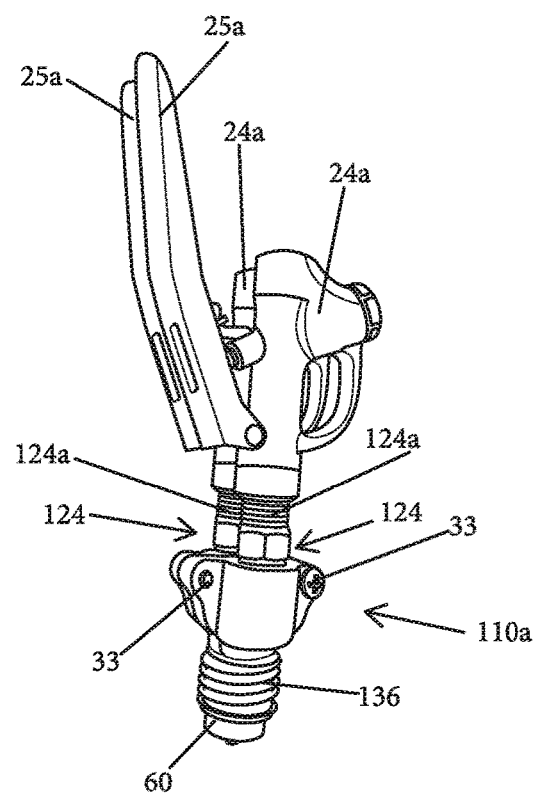
FIG. 24 is another perspective view of the split manifold and trigger valve apparatus of FIG. 23.

Each fluid guide 10a may be coupled with another identical fluid guide 10a to form an assembly defining the split manifold 10 (FIGS. 1, 3-6, 19-20). The split manifold assembly 10 is configured such that the male slip-plugs 32 are insertable into the tube sockets 34 of the push-to-connect manifold 18 simultaneously to simplify the connections between the valve portion 12, split manifold 10, and the push-to-connect manifold 18. As best shown in the illustrated embodiment of FIGS. 12A-12B and 12D-12E, the fluid guide bodies 10a are generally identical to each other in shape and dimension and each includes an interface element, such as mating or interface surface 35, at which the fluid guide bodies can be selectively coupled together. The interface surface 35 of each guide body 10a is shaped and dimensioned to align with an interface surface 35 of another guide body 10a, as best shown in FIG. 19. The split manifold assembly 10 can be fastened with mechanical fasteners 33 between each fluid guide 10a to couple the guides 10a together to form a unitary assembly that may be attached or detached from the valve portion 12 or the push-to-connect manifold 18 as one unit (FIGS. 23-24). The mechanical fastener 33 between each fluid guide 10a may include snaps, screws, or the like which may define a portion of the interface surface 35. In the illustrated embodiment of FIGS. 12A-12E, the mechanical fastener 33 includes holes 33a for screws or bolts to pass through to secure one fluid guide 10a to the other and includes guides or studs 33b to enter into and mate with stud-receiving holes 33c to guide the mating of the fluid guides 10a together. The fluid guides 10a of the split manifold assembly 10 can be separated such that one guide 10a may be replaced with a new or different guide 10a to accommodate a new or different reactive fluid while the other guide 10a is unchanged. When fluid guide bodies 10a are assembled together, the mechanical fasteners 33 and interface surfaces 35 cooperate to resist movement of the fluid guide bodies 10a relative to each other.

The use of a push-to-connect manifold 18 and two-piece split manifold assembly 10 facilitates the assembly of the multi-component fluid mixing and dispensing manifold system 11 from mostly off-the-shelf components that are already mass-produced for many different applications, which can drastically reduce the cost of producing a multi-component fluid mixing and dispensing system. For example, each fluid guide 10a of the two-piece split manifold assembly 10 may be threadedly and sealingly engaged with a respective fluid valve 24 at its downstream end 24b, prior to securing the fluid guides 10a together to form the split manifold assembly 10. It will be appreciated that, because of their geometries and dimensions causing interference, it would not be possible to threadedly engage two fluid valves 24 to respective male threaded inlets 31 of the fluid guides 10a if the fluid guides 10a are already secured together. Lever 25a can then be attached to the respective valve rods 25 of the fluid valves 24, and the push-to-connect manifold 18 can then be attached to the male slip-plugs 32 of the fluid guides 10a. In this way, fluid valves 24 may be standard off-the-shelf products that each carry just one reactive fluid to a respective fluid guide 10a.

The push-to-connect manifold 18 directs the fluids through respective fluid discharge orifices 26 and through respective one-way check valves 64 of a crossover prevention valve 60, which is described below in more detail (FIGS. 5-6 and 14A-14E). Only downstream of the crossover prevention valve 60 do the reactive fluids mix and pass through dispensing nozzle 16, which may include a static mixer to provide further mixing of the fluids before they reach a dispersing tip 200 as described below. This arrangement allows the more costly components of the multi-component fluid mixing and dispensing system 11 to be made from less costly off-the-shelf components than would be possible from custom-made valves and other components, and to be used and reused essentially indefinitely because they remain isolated from mixed reactive fluids at all times during use, allowing them to be more easily cleaned when desired. The split manifold assembly 10 and push-to-connect manifold 18 can also be used and reused many times, but may also be made from lower cost materials that can be considered disposable instead of cleaning, if desired. Even the crossover prevention valve 60 may be used and reused multiple times, as described in commonly-owned U.S. Pat. No. 10,639,656, issued May 5, 2020, which is hereby incorporated herein by reference in its entirety.

In another embodiment, as illustrated in FIGS. 21-24, a split manifold 110 is formed by an assembly 110a of a first fluid guide 130a and a second fluid guide 130b that coordinate to form the split manifold assembly 110a. Each fluid guide 130a and 130b include a respective fluid passageway 122a, 122b. Each fluid guide 130a and 130b includes substantially one semi-cylindrical half of a male threaded distal end portion 136a and 136b which together form a male threaded assembly 136. The male threaded assembly 136 is configured to threadedly engage female threads at the inlet end portion 16a of the dispensing nozzle 16, so that the dispensing nozzle 16 also serves to secure the distal end portions 136a, 136b together while sealingly engaged with a crossover prevention valve 60. Each fluid guide 130a and 130b includes an inlet portion to couple to a fluid trigger valve 24a or a valve adapter 124 (FIGS. 23 and 24). The valve adapter 124 includes male threaded end portions on both of its proximal and distal ends. The male threaded end portions are configured to threadedly engage a female threaded distal end 24b of the fluid trigger valve 24a at the proximal end of the valve adapter 124 and to threadedly engage a female threaded end 132 of one of the fluid guides 130a, 130b at the distal end of the valve adapter 124. The use of separate fluid guides 130a, 130b allows for an assembly with different sizes of orifices 126a, 126b if desired, and the separate fluid guides 130a, 130b may also be attached to respective fluid guides 10a (as discussed above) prior to assembly, which can simplify both the assembly and customization processes.

Figure 21:
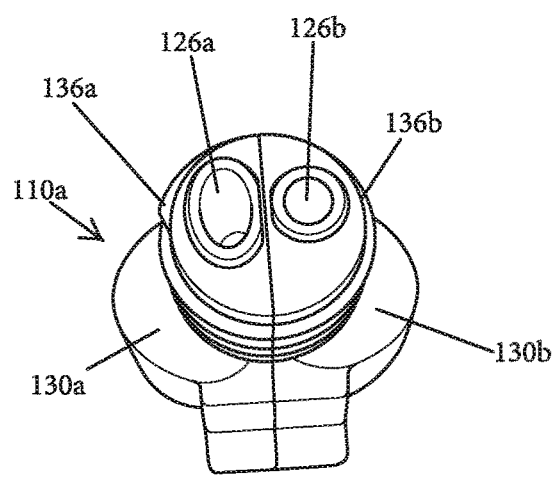
FIG. 21 is a perspective view of another split manifold for a dispensing manifold in accordance with the present invention, having different-size outlet orifices.
Figure 22:
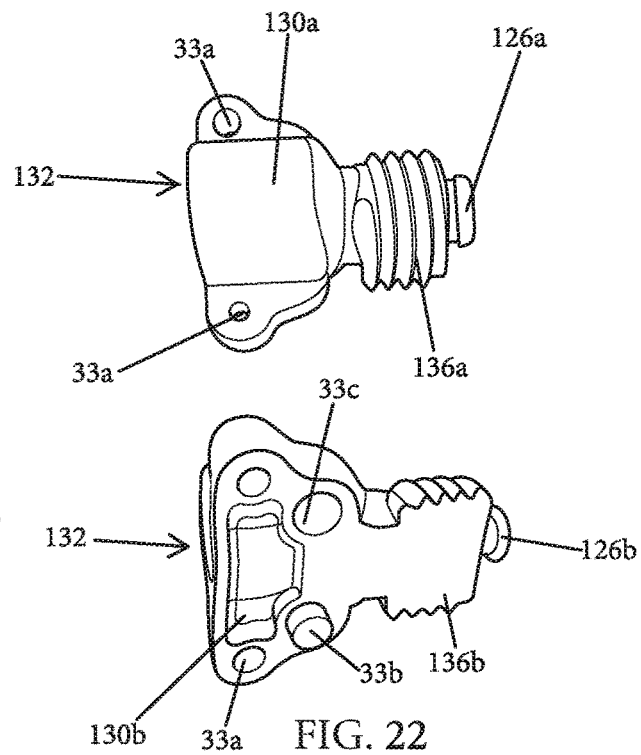
FIG. 22 is an exploded perspective view of the split manifold of FIG. 21.

In the illustrated embodiment of FIGS. 21 and 22, a first orifice 126a defines the distal end of fluid passageway 122a and a second orifice 126b defines the distal end of fluid passageway 122b. First orifice 126a has a diameter different than the second orifice 126b (FIG. 21). For example, the first orifice 126a has a diameter that is selected based on the material characteristics of the composition of the first fluid. The second orifice 126b has a diameter that is selected based on the material characteristics of the composition of the second fluid.

The push-to-connect manifold 18 includes a valve coupling element, such as a quick release resilient mechanical fastener 38, to quickly and securely couple the push-to-connect manifold 18 to the valve portion 12, fluid guide 10a, or split manifold assembly 10 (FIG. 1). As illustrated in FIGS. 1, 3-6, 12A-13D, 18-20, 25, and 29-31, the quick release mechanical fastener 38 includes teeth 38a at an inboard distal end of the fastener 38 configured to engage a tab 40 disposed on a portion of either the valve portion 12, the fluid guide 10a, or other component disposed between the push-to-connect manifold 18 and the valve portion 12. The fastener 38 includes a release tab or depressor lever arm 38b at a proximal end of the fastener 38, that when pressed or depressed toward the push-to-connect manifold 18, disengages the teeth 38a from the tab 40 to release the push-to-connect manifold 18 from the component that it is coupled to.

Figure 25:
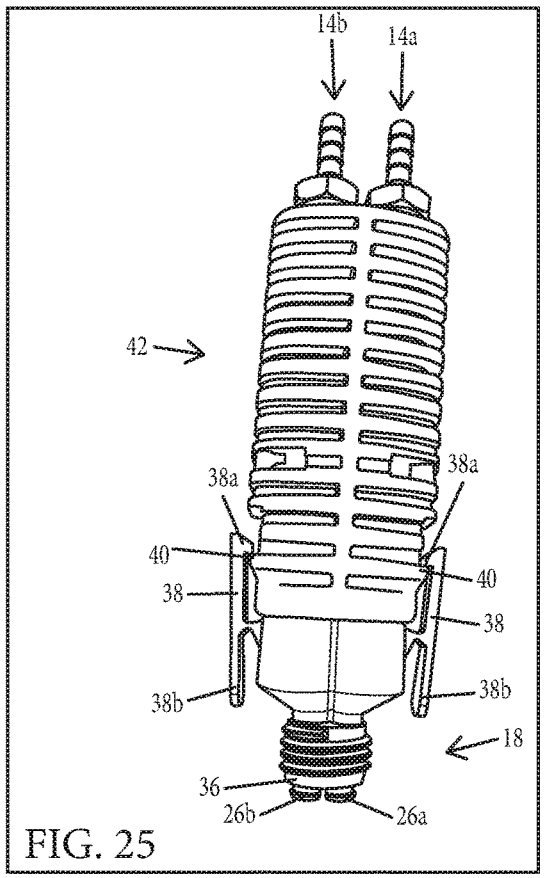
FIG. 25 is a top perspective view of a push-to-connect manifold in accordance with the present invention, shown coupled with a spray gun.
Figure 26:
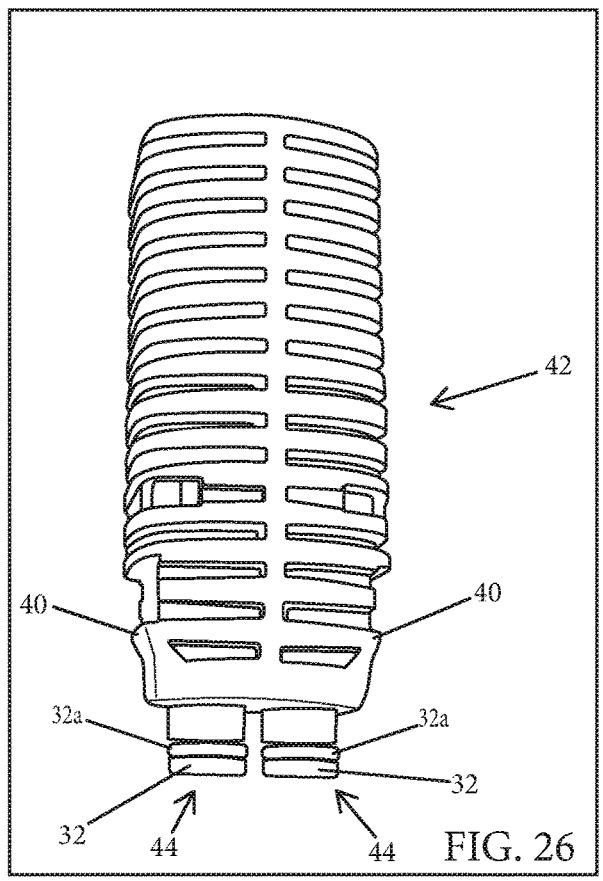
FIG. 26 is a perspective view of the spray gun of FIG. 25, shown with the push-to-connect manifold removed.

In the illustrated embodiment of FIGS. 25 and 26, the push-to-connect manifold 18 is configured to couple directly with a spray gun 42. The spray gun 42 includes two discharge ports 44, each port 44 defined by a male slip-plug 32 that enters into a corresponding female slip socket or tube receptacle 34 of the push-to-connect manifold 18 (FIGS. 25-26). Quick release fasteners 38 of the push-to-connect manifold 18 engage tabs 40 defined by projections on the body of the spray gun 42.

Figure 27:
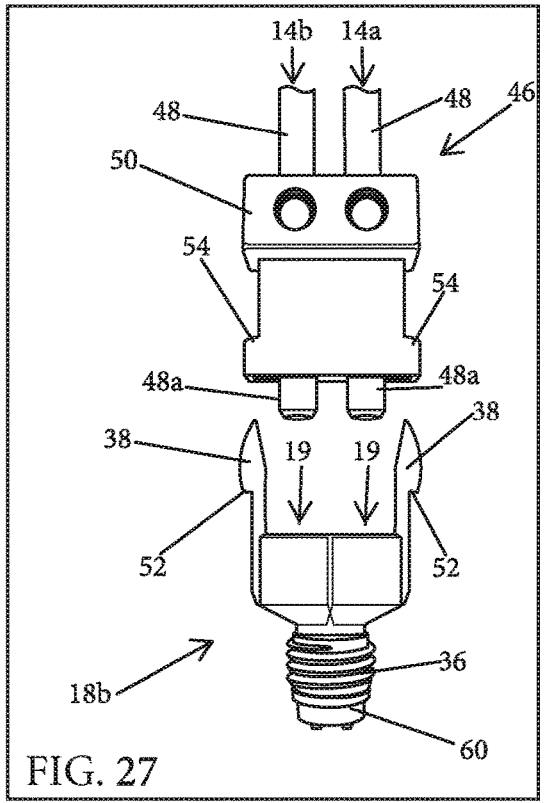
FIG. 27 is an exploded top perspective view of the push-to-connect manifold of FIG. 25, shown fitted with a crossover prevention valve and separated from a pair of fluid discharge tubes.
Figure 28:
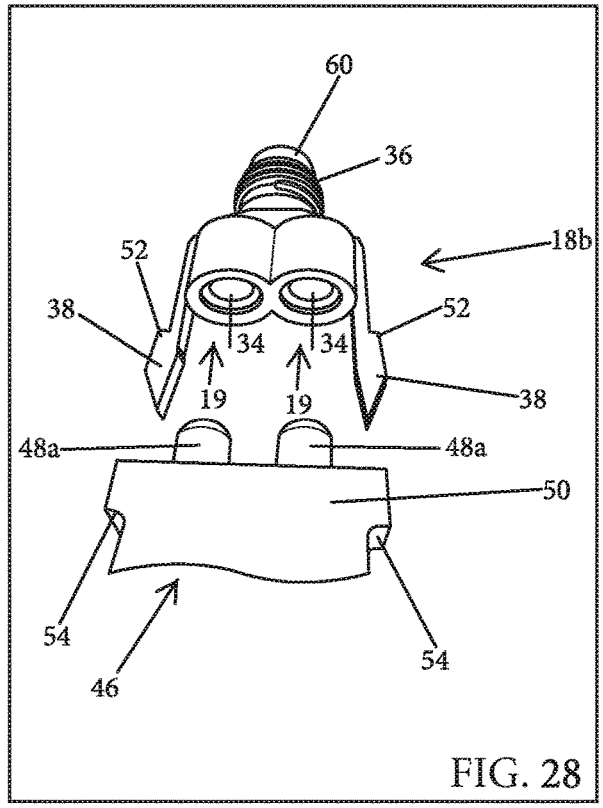
FIG. 28 is another perspective view of the push-to-connect manifold, crossover prevention valve, and fluid discharge tubes of FIG. 27.

In the illustrated embodiment of FIGS. 27-28, a push-to-connect manifold 18b is configured to couple with a spray gun 46 having two elongated discharge tubes 48 coupled together with a coupler 50. The coupler 50 is disposed proximate the discharge end 48a of the discharge tubes 48, leaving at least an end portion of the discharge tubes 48 extending beyond the coupler 50 to be insertable into the female slip sockets 34 of the push-to-connect manifold 18b. Quick release mechanical fasteners 38 disposed on the push-to-connect manifold 18b include teeth 52 disposed at an outboard distal end of the fastener 38. The teeth 52 are configured to enter into the coupler 50 disposed on the spray gun 46 and engage tabs 54 disposed on the coupler 50. The teeth 52 may be pressed or depressed toward the spray gun 46 to disengage the teeth 52 from the tabs 54 to release the push-to-connect manifold 18b from the spray gun 46 for removal.

The split manifold 10 or push-to-connect manifold 18 may include a crossover prevention valve 60, which is more fully described in commonly-owned U.S. Pat. No. 10,639,656, issued May 5, 2020, which is hereby incorporated herein by reference in its entirety (in particular, see FIGS. 5-6 and 14A-14E thereof). As illustrated in FIGS. 5 and 6 of the present application, crossover prevention valve 60 is fitted between the distal end portion 36 of the push-to-connect manifold 18 and the dispensing nozzle 16 and provides additional protection from the two fluids reacting proximate the valve portion 12 split manifold 10, or push-to-connect manifold 18, which could clog or stop the valve portion 12 split manifold 10, or manifold 18 and require cleaning or maintenance. The crossover prevention valve 60 includes a valve body 62 defining or supporting a pair of one-way check valves 64, the valves 64 permitting the fluids to flow out into a mixing chamber 66 defined by the crossover prevention valve 60 and a proximal end portion 16a of dispensing nozzle or discharge tip 16 (FIGS. 1 and 4-6), but which valves 64 preclude any flow reversal (i.e., from the mixing chamber 66 into the valve body 12) even under significant pressure differentials, in part by closing more tightly in response to elevated downstream pressures. This arrangement permits the mixing and dispensing system 11 to be operated such that reactant fluids in mixing chamber 66 can be left to cure, without clogging the valve body's fluid passageways, while facilitating a quick change of the split manifold 10, push-to-connect manifold 18, or the dispensing nozzle 16 to resume dispensing fresh reactant fluids.

The dispensing nozzle 16 may include a dispersing tip 200 that disperses the fluid mixture in a desired spray or discharge pattern (FIGS. 1 and 4-6). The dispersing tip 200 is configurable to provide a desired spray pattern, uniformity of material, or dispersal rate of the mixed fluid based on a function of the material characteristics of the composition of the mixed fluid to be dispersed. An exemplary dispersing tip 200 is described in commonly owned U.S. provisional application Ser. No. 62/946,662, filed Dec. 11, 2019, which is hereby incorporated herein by reference in its entirety, and from which U.S. patent application Ser. No. 17/119,054, filed Dec. 11, 2020 claims priority.

Figure 29:
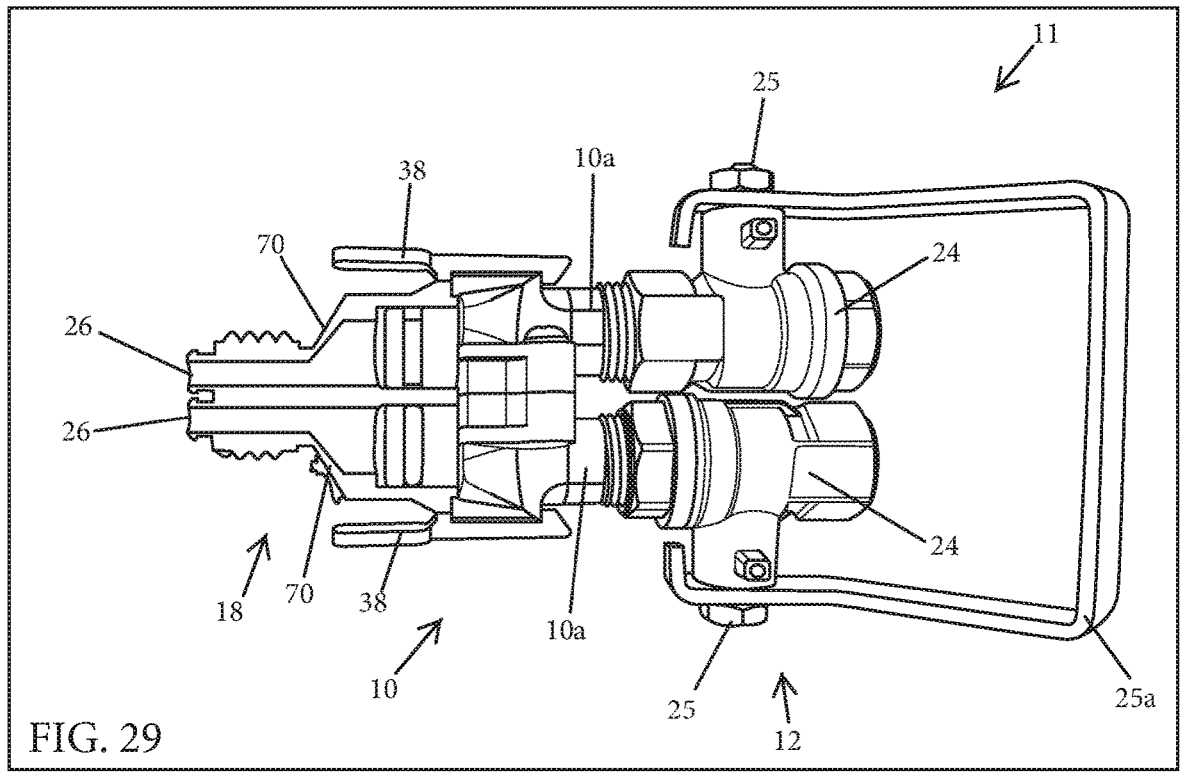
FIG. 29 is a sectional view of a push-to-connect manifold coupled with a split manifold and a valve body to form a dispensing manifold in accordance with the present invention.
Figure 30:
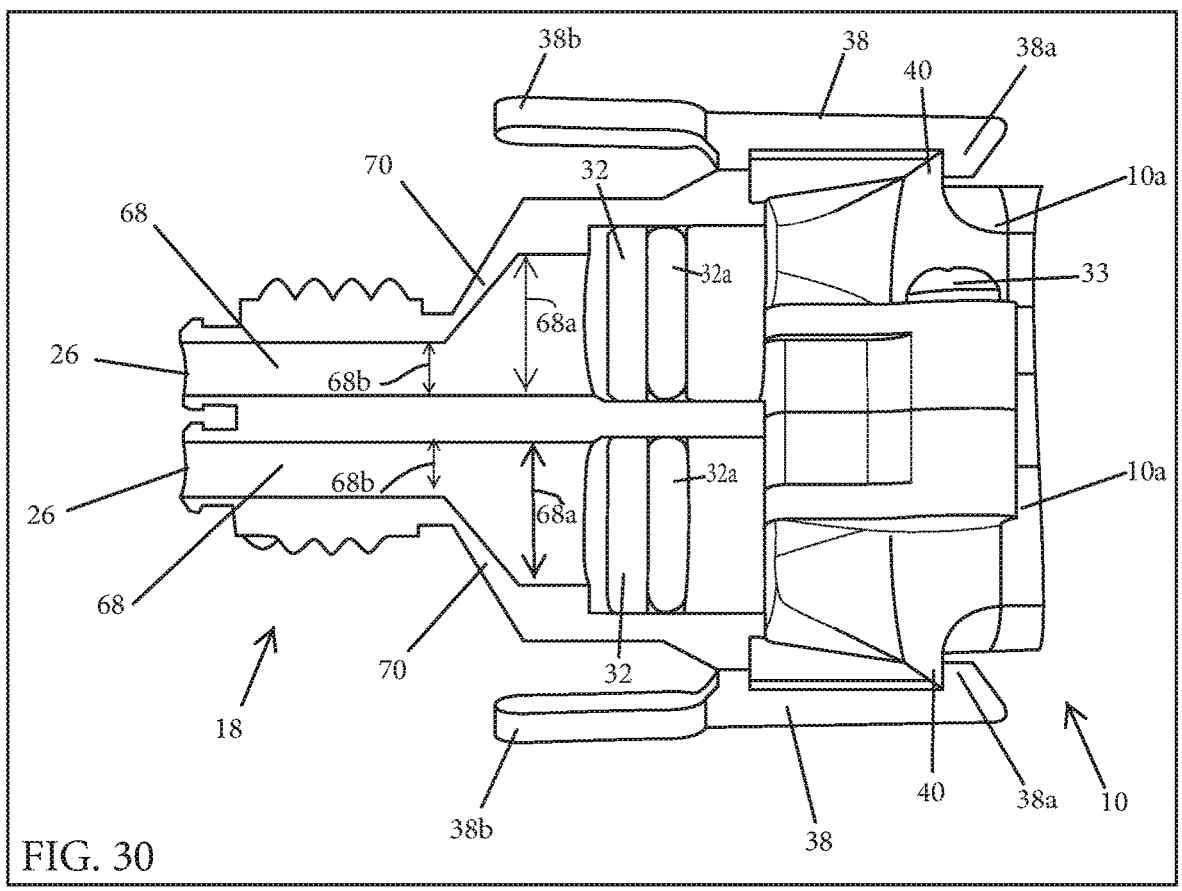
FIG. 30 is a sectional view of the push-to-connect manifold of FIG. 29 attached to the split manifold.
Figure 31:
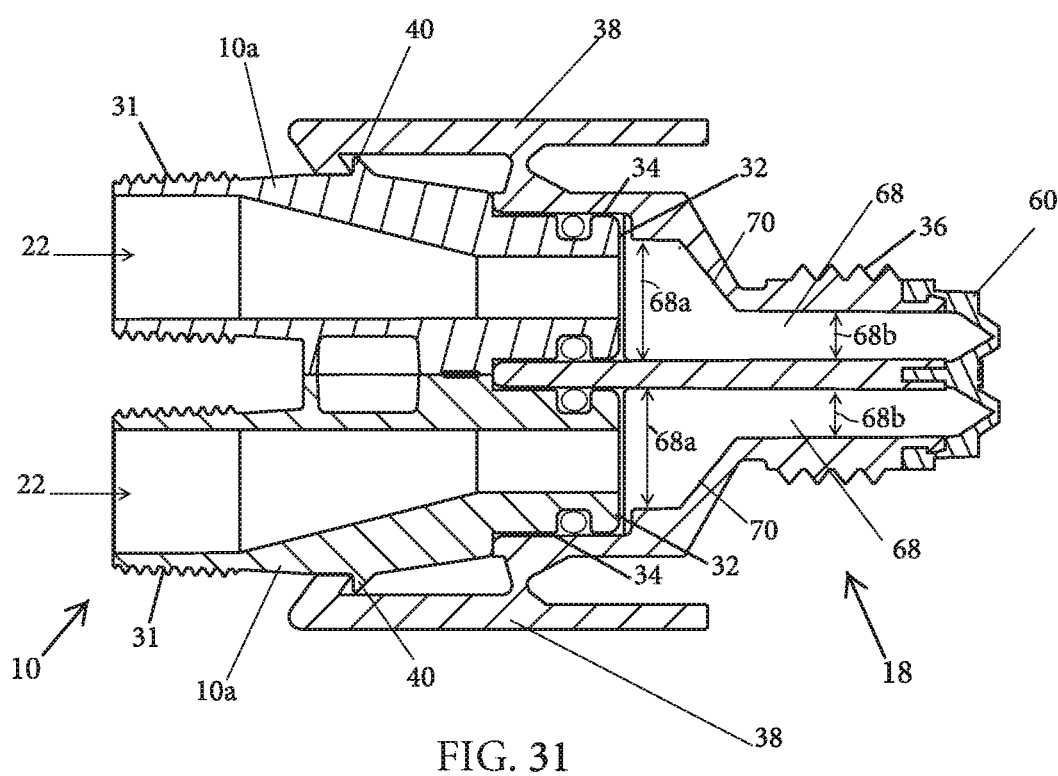
FIG. 31 is a sectional view of the split manifold and push-to-connect manifold of FIGS. 1 and 30, including a crossover prevention valve.

The push-to-connect manifold 18 includes diverting fluid passageways 68 to divert or direct the fluid inside the respective fluid passageway 68 toward a center line of the dispensing tip 16. (FIGS. 29-31). In the illustrated embodiment, the fluid passageway 68 includes a ramp 70 angled toward a centerline of the push-to-connect manifold 18 to direct fluid from the outboard portion of the push-to-connect manifold 18 toward the centerline of the push-to-connect manifold 18 and thereby the centerline of the dispensing tip 16. The ramp 70 begins at an initial diameter 68*a* of the flow passageway 68 and gradually decreases the diameter of the fluid passageway 68 until it reaches a final diameter 68*b* (FIGS. 30-31). The final diameter 68*b* of the fluid passageway 68 is substantially equal to the inner diameter of the discharge orifice 26 corresponding to that fluid passageway. The geometry of the diverting fluid passageways 68 is selected based on a function of material characteristics of the composition of the fluid being directed through that fluid passageway. The geometry of the diverting fluid passageways 68 may be selected such that the fluid is substantially unrestricted while passing through the push-to-connect manifold 18.

Accordingly, the split manifold of the present invention provides a disposable fluid guide for independently directing two reactive fluids from a spray gun, dispensing manifold, or valve to a dispensing tip to reduce or eliminate cleaning time for cleaning a clogged dispensing manifold valve and reduce the possibility that the reactive fluids will interact and react near or at the dispensing manifold valve which may clog or stop the dispensing manifold and require cleaning or replacement of the dispensing manifold, which typically requires time, tools, and effort. Instead of cleaning components, a user can remove the split manifold, valves, or push-to-connect manifold and simply replace that component with a respective new or clean component which reduces down time while operating the dispensing manifold. The split manifold may be adapted for use with various types of dispensing manifolds, spray guns, and valves. Additional features include a push-to-connect manifold extension to extend the reach of the dispensing manifold, independent fluid directing guides that can be individually removed and replaced, and quick release mechanical fasteners to quickly and securely couple the push-to-connect manifold to the dispensing manifold, the split manifold, or to the dispensing tip.

Changes and modifications in the specifically described embodiments can be carried out without departing from the principles of the present invention, which is intended to be limited only by the scope of the appended claims, as interpreted according to the principles of patent law, including the doctrine of equivalents.

The embodiments of the invention in which an exclusive property is claimed are defined as follows:

1. A manifold system for directing separate reactive fluids from separate valves of a valve assembly toward a dispensing tip, said manifold system comprising:
   a manifold assembly comprising a plurality of fluid guide bodies, each fluid guide body defining an independent fluid passageway having (i) a fluid inlet for receiving a respective one of the reactive fluids from a respective one of the valves, and (ii) a fluid outlet for discharging the respective reactive fluid to the dispensing tip;
   each fluid guide body comprising:
      an interface portion for selectively coupling to another of said fluid guide bodies;
      a valve attachment portion for removably securing said fluid guide body to a respective one of the separate valves; and
      a discharge port defining a respective downstream portion of said manifold assembly, wherein said discharge port is configured to be in fluid communication with the dispensing tip;
   wherein said independent fluid passageways are configured to convey the respective reactive fluids through said manifold assembly without mixing; and
   wherein said fluid guide bodies are identical to one another and said interface portions each comprise an interface surface configured to selectively mate with the interface surface of another of said fluid guide bodies.

2. The manifold system of claim 1, wherein each of said valve attachment portions comprises a threaded portion disposed at said fluid inlet and configured to threadedly engage the respective valve.

3. The manifold system of claim 1, further comprising a push-to-connect manifold coupled to said discharge ports, said push-to-connect manifold comprising a threaded region for threadedly engaging the dispensing tip.

4. The manifold system of claim 3, wherein said push-to-connect manifold comprises two manifold portions each comprising a respective portion of said threaded region, wherein said respective portions of said threaded region cooperate to form a substantially continuous thread.

5. The manifold system of claim 1, further comprising a crossover prevention valve disposed between said manifold assembly and the dispensing tip, said crossover prevention valve comprising a unitary body having a plurality of independent fluid passageways each corresponding to said independent fluid passageway of each of said plurality of fluid guide bodies.

6. A manifold system, for directing separate reactive fluids from separate valves of a valve assembly toward a dispensing tip, said manifold system comprising:
   a manifold assembly comprising a plurality of fluid guide bodies, each fluid guide body defining an independent fluid passageway having (i) a fluid inlet for receiving a respective one of the reactive fluids from a respective one of the valves, and (ii) a fluid outlet for discharging the respective reactive fluid to the dispensing tip;
   each fluid guide body comprising:
      an interface portion for selectively coupling to another of said fluid guide bodies:
      a valve attachment portion for removably securing said fluid guide body to a respective one of the separate valves; and
      a discharge port defining a respective downstream portion of said manifold assembly, wherein said discharge port is configured to be in fluid communication with the dispensing tip;
   wherein said independent fluid passageways are configured to convey the respective reactive fluids through said manifold assembly without mixing;
   wherein each of said discharge ports comprises a slip-plug disposed on a downstream end of each of said plurality of fluid guide bodies, said slip-plug configured to slideably engage a respective slip socket at an upstream end of a push-to-connect manifold.

7. The manifold system of claim 6, further comprising a crossover prevention valve disposed between the downstream end of said manifold system and the dispensing tip, said crossover prevention valve configured to prevent interaction of the fluids at the downstream end of said manifold system.

8. The manifold system of claim 1, wherein said manifold system is releasably removable from the valve assembly at each of said valve attachment portions and releasably removable from the dispensing tip at said discharge ports.

9. The manifold system of claim 6, wherein each of said fluid guide bodies are identical and said interface portion of each of said fluid guide bodies comprises an interface surface configured to selectively mate with the interface surface of another of said fluid guide bodies.

10. The manifold system of claim 9, wherein said interface portion of each of said fluid guide bodies further comprises a stud and hole arrangement configured to mate with a matching stud and hole arrangement of another of said fluid guide bodies.

11. A method of assembling a dispensing manifold for directing reactive fluids from valves of a valve assembly to a dispensing tip, said method comprising:

rotatably and threadably coupling upstream ends of separate first and second fluid guide bodies to downstream ends of respective separate first and second fluid valves, each fluid guide body defining an independent fluid passageway having (i) a fluid inlet for receiving a respective one of the reactive fluids from a respective one of the first and second fluid valves, and (ii) a fluid outlet for discharging the respective reactive fluid to the dispensing tip, and each fluid guide body comprising:
an interface portion for selectively coupling to another of the fluid guide bodies;
a valve attachment portion for removably securing the fluid guide body to a respective one of the separate valves; and
a discharge port defining a respective downstream portion of the manifold assembly, wherein the discharge port is configured to releasably couple to the dispensing tip;
wherein the independent fluid passageways are configured to convey the respective reactive fluids through the manifold assembly without mixing;

engaging respective interface portions of the first and second fluid guide bodies with one another, wherein the fluid guide bodies are identical to one another and said interface portions each comprise an interface surface configured to selectively mate with the interface surface of another of said fluid guide bodies;

securing the first fluid guide body to the second fluid guide body with a mechanical fastener;

slideably engaging the discharge ports of the first and second fluid guide bodies in a longitudinal direction with respective upstream end portions of a push-to-connect manifold; and coupling an actuator to the first and second fluid valves, wherein the actuator is operable to simultaneously actuate the first and second fluid valves between open and closed positions.

12. The method of claim 11, wherein said engaging respective interfacing surfaces comprises simultaneously inserting a stud along the first fluid guide body's interface portion into a hole formed in the second fluid guide body's interface portion while inserting a stud along the second fluid guide body's interface portion into a hole formed in the first fluid guide body's interface portion.

13. A manifold system for directing separate reactive fluids from separate valves of a valve assembly toward a dispensing tip, said manifold system comprising:

a manifold assembly comprising a plurality of fluid guide bodies, each fluid guide body defining an independent fluid passageway having (i) a fluid inlet for receiving a respective one of the reactive fluids from a respective one of the valves, and (ii) a fluid outlet for discharging the respective reactive fluid to the dispensing tip;
each fluid guide body comprising:
an interface portion for selectively coupling to another of said fluid guide bodies;
a valve attachment portion for removably securing said fluid guide body to a respective one of the separate valves; and
a discharge port defining a respective downstream portion of said manifold assembly, wherein said discharge port is configured to be in fluid communication with the dispensing tip;
a push-to-connect manifold coupled to said discharge ports and comprising a threaded region for threadedly engaging the dispensing tip, said push-to-connect manifold comprising two manifold portions each forming a respective portion of said threaded region, wherein said respective portions of said threaded region cooperate to form a substantially continuous thread;
wherein said independent fluid passageways are configured to convey the respective reactive fluids through said manifold assembly without mixing.

14. The manifold system of claim 13, wherein each of said fluid guide bodies comprises a slip-plug at said discharge port, and said push-to-connect manifold comprises a slip-socket configured to slidably receive a respective one of said slip-plugs.

* * * * *

UNITED STATES PATENT AND TRADEMARK OFFICE
CERTIFICATE OF CORRECTION

| | | |
|---|---|---|
| PATENT NO. | : 11,911,787 B1 | Page 1 of 1 |
| APPLICATION NO. | : 16/995442 | |
| DATED | : February 27, 2024 | |
| INVENTOR(S) | : Gary Hammerlund | |

It is certified that error appears in the above-identified patent and that said Letters Patent is hereby corrected as shown below:

In the Specification

Column 4, Line 31:
"FIG. 1:" should be --FIG. 1;--

Column 5, Line 32:
"orifices:" should be --orifices;--

Column 5, Line 47:
"tubes:" should be --tubes;--

In the Claims

Column 12, Claim 6:
Line 26, "system, for" should be --system for--
Line 37, "bodies:" should be --bodies;--

Signed and Sealed this
Twenty-sixth Day of March, 2024

Katherine Kelly Vidal
*Director of the United States Patent and Trademark Office*